US007223572B1

(12) United States Patent
Gunji et al.

(10) Patent No.: US 7,223,572 B1
(45) Date of Patent: May 29, 2007

(54) *METHYLOPHILUS METHYLOTROPHUS* HAVING ENHANCED DIHYDRODIPICOLINATE SYNTHASE AND/OR ASPARTOKINASE ACTIVITY FOR L-AMINO ACID PRODUCTION

(75) Inventors: Yoshiya Gunji, Kawasaki (JP); Hisashi Yasueda, Kawasaki (JP); Shinichi Sugimoto, Kawasaki (JP); Nobuharu Tsujimoto, Kawasaki (JP); Megumi Shimaoka, Kawasaki (JP); Yuri Miyata, Kawasaki (JP); Manami Oba, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/926,299

(22) PCT Filed: Apr. 7, 2000

(86) PCT No.: PCT/JP00/02295

§ 371 (c)(1),
(2), (4) Date: Oct. 9, 2001

(87) PCT Pub. No.: WO00/61723

PCT Pub. Date: Oct. 19, 2000

(30) Foreign Application Priority Data

Apr. 9, 1999 (JP) ................................ 11/103143
Jun. 16, 1999 (JP) ................................ 11/169447
Dec. 24, 1999 (JP) ................................ 11/368097

(51) Int. Cl.
*C12P 13/04* (2006.01)
*C12N 1/20* (2006.01)
*C07H 21/04* (2006.01)
*C12N 9/12* (2006.01)
*C12N 9/88* (2006.01)

(52) U.S. Cl. .................. 435/106; 435/115; 435/252.1; 435/252.3; 435/194; 435/232; 536/23.1; 536/23.2; 536/23.7

(58) Field of Classification Search ................ 435/106, 435/115, 243, 252.3, 194–232; 536/23.2–23.7
See application file for complete search history.

(56) References Cited

U.S. PATENT DOCUMENTS 4,824,786 A 4/1989 Hanson et al.
5,939,307 A * 8/1999 Wang et al. ........... 435/252.33
6,040,160 A * 3/2000 Kojima et al. .............. 435/115
6,303,381 B1 10/2001 Gunji et al.
6,350,596 B2 * 2/2002 Iomantas et al. ........... 435/108

FOREIGN PATENT DOCUMENTS

EP 35831 9/1981
EP 37273 10/1981
EP 0435132 7/1991
EP 0 857 784 8/1998
JP 53-34987 3/1978
JP 1-235595 9/1989
WO 87 02984 5/1987
WO WO 95/16042 6/1995
WO 96/41871 12/1996

OTHER PUBLICATIONS

Branden et al. "Introduction to Protein Structure", Garland Publishing Inc., New York, 1991, p. 247.*

Witkowski et al. (1999) Biochemistry 38:11643-11650.*

Voet et al. "Biochemistry, 2nd Ed.," John Wiley and Sons, Inc., New York, 1995, pp. 762-763.*

"Current Protocols in Molecular Biology" Ausubel et al., John Wiley and Sons, Inc., New York, 1993, Unit 2.9A, pp. 1-2 and Unit 2.10, pp. 1-16.*

Proc Natl Acad Sci (1982) 79:4256-4259, De Maeyer et al.*

J. D. Cirillo, et al., Molecular Microbiology, vol. 11, No. 4, pp. 629-639, XP-002907355, "Isolation and Characterization of the Aspartokinase and Aspartate Semialdehyde Dehydrogenase Operon from Mycobacteria", 1994.

Database EMBL Online !, Database Accession No. Z17372, pp. 1-3, XP-002244623, Aug. 9, 1994.

Database EMBL Online !, Database Accession No. P41403, pp. 1-2, XP-002244624, Nov. 1, 1995.

Derwent Abstracts, AN 1993-297465, XP-002244625, JP 05-207866, Aug. 20, 1993.

Kim, et al., "Creating auxotrophic mutants in *Methylophilus methylotrophus* AS1 by combining electroporation and chemical mutagenesis", Applied Microbiology and Biotechnology, vol. 48, No. 1, (1997), pp. 105-108.

J.D. Windass et al.: "Improved converstion of methanol to single-cell protein by *Methylophilus methylorophus*" NATURE, vol. 287, pp. 396-401 Oct. 2, 1980.

Frederick J. Schendel, et al.: "Cloning and Nucleotide Sequence of the Gene Coding for Aspartokinase II from a Thermophilic Methylotrophic *Bacillus* sp." Applied and En-Vironmental Microbiology, vol. 58, No. 9, pp. 2806-2814 Sep. 1992.

(Continued)

*Primary Examiner*—David J. Steadman
(74) *Attorney, Agent, or Firm*—Cermak & Kenealy, LLP; Shelly Guest Cermak

(57) ABSTRACT

An L-amino acid is produced by culturing a *Methylophilus* bacterium which can grow by using methanol as a main carbon source and has L-amino acid-producing ability, for example, a *Methylophilus* bacterium in which dihydrodipicolinate synthase activity and aspartokinase activity are enhanced by transformation through introduction into cells, of a DNA coding for dihydrodipicolinate synthase that does not suffer feedback inhibition by L-lysine and a DNA coding for aspartokinase that does not suffer feedback inhibition by L-lysine, or a *Methylophilus* bacterium made to be casamino acid auxotrophic, in a medium containing methanol as a main carbon source, to produce and accumulate an L-amino acid in culture, and collecting the L-amino acid from the culture.

24 Claims, 5 Drawing Sheets

OTHER PUBLICATIONS

Tung T. Hoang, et al.: "Molecular genetic analysis of the region containing the essential *Pseudomonas aeruginosa asd* gene encoding aspartate-beta-semialdehyde dehydrogenase" MICROBIOLOGY, vol. 143, Part 3, pp. 899-907 Mar. 1997.

Yoshihiro Yamamoto et al.: "Construction of a Contiguous 874-kb Sequence of the *Escherichia coli*-K12 Genome corresponding to 50.5-68.8 min on the Linkage Map and Analysis of Its Sequence Features" DNA Research, vol. 4, No. 2, pp. 91-113 Apr. 28, 1997.

S. Bonnassie et al.: "Nucleotide sequence of the dapA gene from *Corynebacterium glutamicum*" Nucleic Acids Research, vol. 18, No. 21, p. 6421 Nov. 11, 1990.

J. Bouvier et al.: "Nucleotide Sequence and Expression of the *Escherichia coli dap*B Gene" The Journal of Biological Chemistry, vol. 259, No. 23, pp. 14829-14834 Dec. 10, 1984.

Linda C. Dekkers et al. "A site-specific recombinase is required for competitive root colonization by *Pseudomonas fluorescens* WCS365" Proceedings of the National Academy of Sciences, USA, vol. 95, No. 12, pp. 7051-7056 Jun. 9, 1998.

P. Kerney et al: "Regulations and routes of biosynthesis of serin and arginine in *Methylophilus methylotrophus* ASI" FEMS Microbiology Letters, vol. 42, Nos. 2-3, pp. 109-112 Jul. 1987.

Office Action by the Chinese Patent Office for Chinese Patent Appl. No. 00806019.3 (Jan. 16, 2004).

* cited by examiner

*METHYLOPHILUS METHYLOTROPHUS* HAVING ENHANCED DIHYDRODIPICOLINATE SYNTHASE AND/OR ASPARTOKINASE ACTIVITY FOR L-AMINO ACID PRODUCTION

TECHNICAL FIELD

The present invention relates to techniques in the field of microbial industry. In particular, the present invention relates to a method for producing an L-amino acid by fermentation, and a microorganism used in the method.

BACKGROUND ART

Amino acids such as L-lysine, L-glutamic acid, L-threonine, L-leucine, L-isoleucine, L-valine and L-phenylalanine are industrially produced by fermentation by using microorganisms that belong to the genus *Brevibacterium, Corynebacterium, Bacillus, Escherichia, Streptomyces, Pseudomonas, Arthrobacter, Serratia, Penicillium, Candida* or the like. In order to improve the productivity, strains isolated from nature or artificial mutants thereof have been used as these microorganisms. Various techniques have been disclosed for enhancing activities of L-glutamic acid biosynthetic enzymes by using recombinant DNA techniques, to increase the L-glutamic acid-producing ability.

The productivity of L-amino acids has been considerably increased by breeding of microorganisms such as those mentioned above and the improvement of production methods. However, in order to meet further increase in the demand in future, development of methods for more efficiently producing L-amino acids at lower cost have still been desired.

As methods for producing amino acids by fermentation of methanol which is a fermentation raw material available in a large amount at a low cost, there have conventionally known methods using microorganisms that belong to the genus *Achromobacter* or *Pseudomonas* (Japanese Patent Publication (Kokoku) No. 45-25273/1970), *Protaminobacter* (Japanese Patent Application Laid-open (Kokai) No. 49-125590/1974), *Protaminobacter* or *Methanomonas* (Japanese Patent Application Laid-open (Kokai) No. 50-25790/1975), *Microcyclus* (Japanese Patent Application Laid-open (Kokai) No. 52-18886/1977), *Methylobacillus* (Japanese Patent Application Laid-open (Kokai) No. 4-91793/1992), *Bacillus* (Japanese Patent Application Laid-open (Kokai) No. 3-505284/1991) and so forth.

So far, however, no method has been known for producing L-amino acids by using *Methylophilus* bacteria. Although methods described in EP 0 035 831 A, EP 0 037 273 A and EP 0 066 994 A have been known as methods for transforming *Methylophilus* bacteria by using recombinant DNA, applying recombinant DNA techniques to improvement of amino acid productivity of *Methylophilus* bacteria has not been known.

DISCLOSURE OF THE INVENTION

The object of the present invention is to provide a novel L-amino acid-producing bacterium and a method for producing an L-amino acid by using the L-amino acid-producing bacterium.

As a result of the present inventors' efforts devoted to achieve the aforementioned object, they found that *Methylophilus* bacteria were suitable for producing L-amino acids. Further, although it has conventionally been considered difficult to obtain auxotrophic mutants of *Methylophilus* bacteria (FEMS Microbiology Rev. 39, 235–258 (1986) and Antonie van Leeuwenhoek 53, 47–53 (1987)), the present inventors have succeeded in obtaining auxotrophic mutants of said bacteria. Thus, the present invention has been accomplished.

That is, the present invention provides the followings.

(1) A *Methylophilus* bacterium having L-amino acid-producing ability.

(2) The *Methylophilus* bacterium according to (1), wherein the L-amino acid is L-lysine, L-valine, L-leucine, L-isoleucine or L-threonine.

(3) The *Methylophilus* bacterium according to (1), which has resistance to an L-amino acid analogue or L-amino acid auxotrophy.

(4) The *Methylophilus* bacterium according to (1), wherein L-amino acid biosynthetic enzyme activity is enhanced.

(5) The *Methylophilus* bacterium according to (1), wherein dihydrodipicolinate synthase activity and aspartokinase activity are enhanced, and the bacterium has L-lysine-producing ability.

(6) The *Methylophilus* bacterium according to (1), wherein dihydrodipicolinate synthase activity is enhanced, and the bacterium has L-lysine-producing ability.

(7) The *Methylophilus* bacterium according to (1), wherein aspartokinase activity is enhanced, and the bacterium has L-lysine-producing ability.

(8) The *Methylophilus* bacterium according to any one of (5) to (7), wherein an activity or activities of one, two or three of enzymes selected from aspartic acid semialdehyde dehydrogenase, dihydrodipicolinate reductase and diaminopimelate decarboxylase is/are enhanced.

(9) The *Methylophilus* bacterium according to (5), wherein the dihydrodipicolinate synthase activity and the aspartokinase activity are enhanced by transformation through introduction into cells, of a DNA coding for dihydrodipicolinate synthase that does not suffer feedback inhibition by L-lysine and a DNA coding for aspartokinase that does not suffer feedback inhibition by L-lysine.

(10) The bacterium according to (1), wherein activities of aspartokinase, homoserine dehydrogenase, homoserine kinase and threonine synthase are enhanced, and the bacterium has L-threonine-producing ability.

(11) The bacterium according to any one of (1) to (10), wherein the *Methylophilus* bacterium is *Methylophilus methylotrophus*.

(12) A method for producing an L-amino acid, which comprises culturing a *Methylophilus* bacterium as defined in any one of the above (1) to (11) in a medium to produce and accumulate an L-amino acid in culture and collecting the L-amino acid from the culture.

(13) The method according to (12), wherein the medium contains methanol as a main carbon source.

(14) A method for producing bacterial cells of a *Methylophilus* bacterium with an increased content of an L-amino acid, which comprises culturing a *Methylophilus* bacterium as defined in any one of the above (1) to (11) in a medium to produce and accumulate an L-amino acid in bacterial cells of the bacterium.

(15) The method for producing bacterial cells of the *Methylophilus* bacterium according to (14), wherein the L-amino acid is L-lysine, L-valine, L-leucine, L-isoleucine or L-threonine.

(16) A DNA which codes for a protein defined in the following (A) or (B):

(A) a protein which has the amino acid sequence of SEQ ID NO: 6, or (B) a protein which has an amino acid sequences of SEQ ID NO: 6 including substitution, deletion, insertion, addition or inversion of one or several amino acids, and has aspartokinase activity.

(17) The DNA according to (16), which is a DNA defined in the following (a) or (b):

(a) a DNA which has a nucleotide sequence comprising the nucleotide sequence of the nucleotide numbers 510 to 1736 of SEQ ID NO: 5; or (b) a DNA which is hybridizable with a probe having the nucleotide sequence of the nucleotide numbers 510 to 1736 of SEQ ID NO: 5 or a part thereof under a stringent condition, and codes for a protein having aspartokinase activity.

(18) A DNA which codes for a protein defined in the following (C) or (D):

(C) a protein which has the amino acid sequence of SEQ ID NO: 8, or (D) a protein which has an amino acid sequences of SEQ ID NO: 8 including substitution, deletion, insertion, addition or inversion of one or several amino acids, and has aspartic acid semialdehyde dehydrogenase activity.

(19) The DNA according to (18), which is a DNA defined in the following (c) or (d):

(c) a DNA which has a nucleotide sequence comprising the nucleotide sequence of the nucleotide numbers 98 to 1207 of SEQ ID NO: 7; or (d) a DNA which is hybridizable with a probe having the nucleotide sequence of the nucleotide numbers 98 to 1207 of SEQ ID NO: 7 or a part thereof under a stringent condition, and codes for a protein having aspartic acid semialdehyde dehydrogenase activity.

(20) A DNA which codes for a protein defined in the following (E) or (F):

(E) a protein which has the amino acid sequence of SEQ ID NO: 10, or (F) a protein which has an amino acid sequences of SEQ ID NO: 10 including substitution, deletion, insertion, addition or inversion of one or several amino acids, and has dihydrodipicolinate synthase activity.

(21) The DNA according to (20), which is a DNA defined in the following (e) or (f):

(e) a DNA which has a nucleotide sequence comprising the nucleotide sequence of the nucleotide numbers 1268 to 2155 of SEQ ID NO: 9; or (f) a DNA which is hybridizable with a probe having the nucleotide sequence of the nucleotide numbers 1268 to 2155 of SEQ ID NO: 9 or a part thereof under a stringent condition, and codes for a protein having dihydrodipicolinate synthase activity.

(22) A DNA which codes for a protein defined in the following (G) or (H):

(G) a protein which has the amino acid sequence of SEQ ID NO: 12, or (H) a protein which has an amino acid sequences of SEQ ID NO: 12 including substitution, deletion, insertion, addition or inversion of one or several amino acids, and has dihydrodipicolinate reductase activity.

(23) The DNA according to (22), which is a DNA defined in the following (g) or (h):

(g) a DNA which has a nucleotide sequence comprising the nucleotide sequence of the nucleotide numbers 2080 to 2883 of SEQ ID NO: 11; or (h) a DNA which is hybridizable with a probe having the nucleotide sequence of the nucleotide numbers 2080 to 2883 of SEQ ID NO: 11 or a part thereof under a stringent condition, and codes for a protein having dihydrodipicolinate reductase activity.

(24) A DNA which codes for a protein defined in the following (I) or (J):

(I) a protein which has the amino acid sequence of SEQ ID NO: 14, or (J) a protein which has an amino acid sequences of SEQ ID NO: 14 including substitution, deletion, insertion, addition or inversion of one or several amino acids, and has diaminopimelate decarboxylase activity.

(25) The DNA according to (24), which is a DNA defined in the following (i) or (j):

(i) a DNA which has a nucleotide sequence comprising the nucleotide sequence of the nucleotide numbers 751 to 1995 of SEQ ID NO: 13; or (j) a DNA which is hybridizable with a probe having the nucleotide sequence of the nucleotide numbers 751 to 1995 of SEQ ID NO: 13 or a part thereof under a stringent condition, and codes for a protein having diaminopimelate decarboxylase activity.

In the present specification, "L-amino acid-producing ability" refers to ability to accumulate a significant amount of an L-amino acid in a medium or to increase the amino acid content in the microbial cells when a microorganism of the present invention is cultured in the medium.

BEST MODE FOR CARRYING OUT THE INVENTION

<1> Microorganism of the Present Invention

Figure 1:
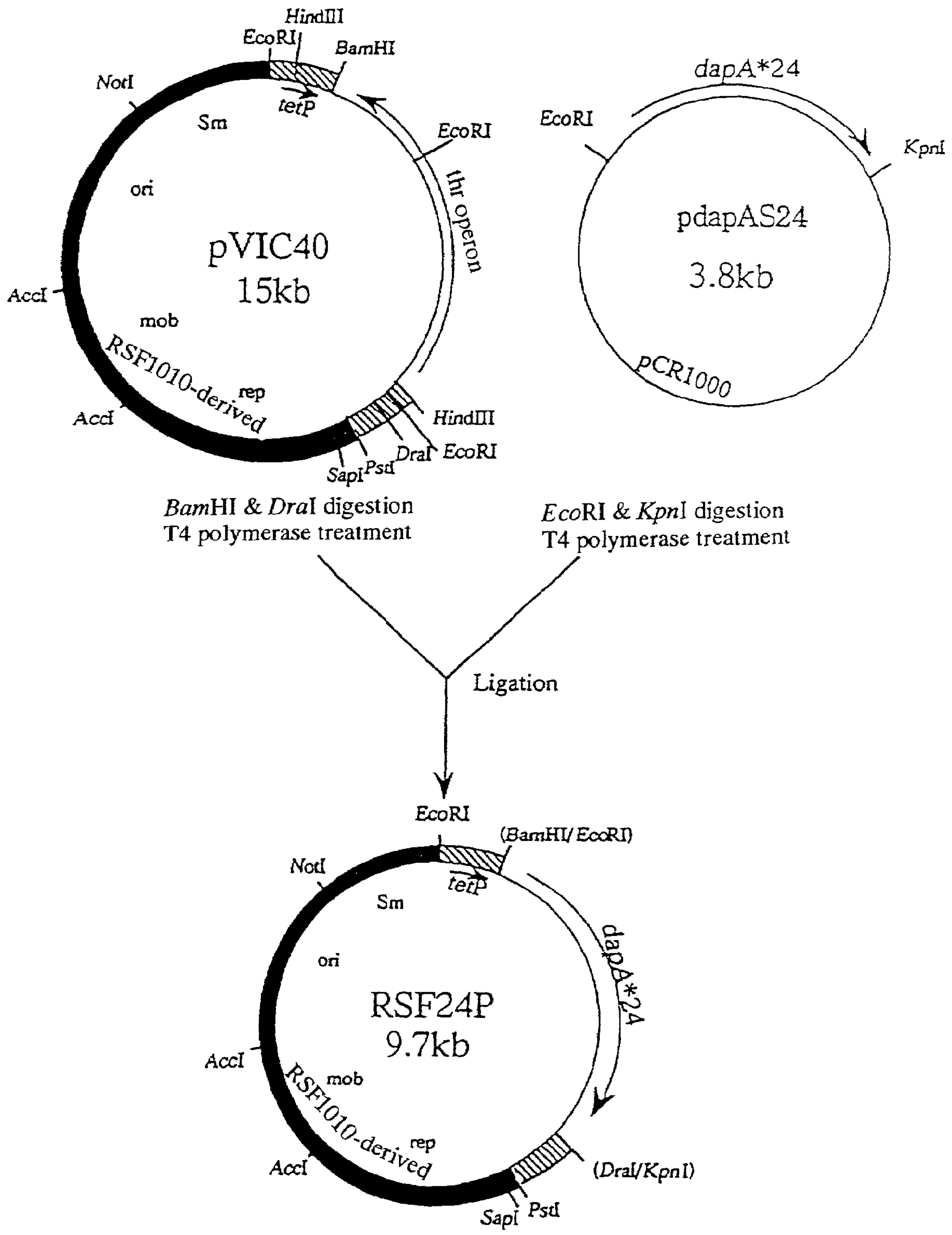
FIG. 1 shows the production process of plasmid RSF24P having a mutant dapA. The "dapA*24" refers to a mutant dapA that codes for a mutant DDPS wherein the 118-histidine residue is replaced with a tyrosine residue.

The microorganism of the present invention is a bacterium belonging to the genus *Methylophilus* and having L-amino acid-producing ability. The *Methylophilus* bacterium of the present invention includes, for example, *Methylophilus methylotrophus* AS1 strain (NCIMB10515) and so forth. The *Methylophilus methylotrophus* AS1 strain (NCIMB10515) is available from National Collections of Industrial and Marine Bacteria (Address: NCIMB Lts., Torry Research Station 135, Abbey Road, Aberdeen AB9 8DG, United Kingdom).

L-Amino acids produced according to the present invention include L-lysine, L-glutamic acid, L-threonine, L-valine, L-leucine, L-isoleucine, L-tryptophan, L-phenylalanine, L-tyrosine and so forth. One or more types of such amino acids may be produced.

*Methylophilus* bacteria having L-amino acid-producing ability can be obtained by imparting L-amino acid-producing ability to wild strains of *Methylophilus* bacteria. In order to impart L-amino acid-producing ability, there can be used methods conventionally adopted for breeding coryneform bacteria, *Escherichia* bacteria or the like, such as those methods for obtaining auxotrophic mutant strains, strains resistant to L-amino acid analogues or metabolic control mutant strains, and methods for producing recombinant strains wherein L-amino acid biosynthetic enzyme activities are enhanced (see “Amino Acid Fermentation”, the Japan Scientific Societies Press [Gakkai Shuppan Center], 1st Edition, published on May 30, 1986, pp. 77 to 100). In breeding of amino acid-producing bacteria, the characteristic such as auxotrophy, L-amino acid analogue resistance and metabolic control mutation may be imparted alone or in combination of two or more. The L-amino acid biosynthetic enzyme activity may be enhanced alone or in combination of two or more. Further, imparting of the characteristic such as auxotrophy, L-amino acid analogue resistance and metabolic control mutation may be combined with enhancement of the L-amino acid biosynthesis enzyme activity.

For example, L-lysine-producing bacteria are bred as mutants exhibiting auxotrophy for L-homoserine or L-threonine and L-methionine (Japanese Patent Publication (Kokoku) Nos. 48-28078/1973 and 56-6499/1981), mutants exhibiting auxotrophy for inositol or acetic acid (Japanese Patent Application Laid-open (Kokai) Nos. 55-9784/1980 and 56-8692/1981), or mutants that are resistant to oxalysine, lysine hydroxamate, S-(2-aminoethyl)-cysteine, γ-methyllysine, α-chlorocaprolactam, DL-α-amino-ε-caprolactam, α-amino-lauryllactam, aspartic acid analogue, sulfa drug, quinoid or N-lauroylleucine.

Further, L-glutamic acid-producing bacteria can be bred as mutants exhibiting auxotrophy for oleic acid or the like. L-Threonine-producing bacteria can be bred as mutants resistant to α-amino-β-hydroxyvaleric acid. L-Homoserine-producing bacteria can be bred as mutants exhibiting auxotrophy for L-threonine or mutants resistant to L-phenylalanine analogues. L-Phenylalanine-producing bacteria can be bred as mutants exhibiting auxotrophy for L-tyrosine. L-Isoleucine-producing bacteria can be bred as mutants exhibiting auxotrophy for L-leucine. L-Proline-producing bacteria can be bred as mutants exhibiting auxotrophy for L-isoleucine.

Furthermore, as mentioned in the examples hereinafter, strains that produce one or more kinds of branched amino acids (L-valine, L-leucine and L-isoleucine) can be obtained as strains exhibiting auxotrophy for casamino acid.

In order to obtain mutants from *Methylophilus* bacteria, the inventors of the present invention first examined details of an optimal mutagenesis condition by using emergence frequency of streptomycin resistant strains as an index. As a result, the maximum emergence frequency of streptomycin resistant strains was obtained when the survival rate after mutagenesis was about 0.5%, and they succeeded in obtaining auxotrophic strains under this condition. They also succeeded in obtaining auxotrophic strains, which had been considered difficult, by largely scaling up the screening of mutants compared with that previously conducted for *E. coli* and so forth.

As described above, since it has been revealed that mutants can be obtained by mutagenizing *Methylophilus* bacteria under a suitable condition, it has become possible to readily obtain desired mutants by suitably setting such a condition that the survival rate after the mutagenesis should become about 0.5%, depending on the mutagenesis method.

Mutagenesis methods for obtaining mutants from *Methylophilus* bacteria include UV irradiation and treatments with mutagenesis agents used for usual mutatagenesis treatments such as N-methyl-N'-nitro-N-nitrosoguanidine (NTG) and nitrous acid. *Methylophilus* bacteria having L-amino acid-producing ability can also be obtained by selecting naturally occurring mutants of *Methylophilus* bacteria.

L-Amino acid analogue-resistant mutants can be obtained by, for example, inoculating mutagenized *Methylophilus* bacteria to an agar medium containing an L-amino acid analogue at a variety of concentrations and selecting strains that form colonies.

Auxotrophic mutants can be obtained by allowing *Methylophilus* bacteria to form colonies on an agar medium containing a target nutrient (for example, L-amino acid), replicating the colonies to an agar medium not containing said nutrient, and selecting strains that cannot grow on the agar medium not containing the nutrient.

Methods for imparting or enhancing L-amino acid-producing ability by enhancing L-amino acid biosynthetic enzyme activity will be exemplified below.

[L-Lysine]

L-Lysine-producing ability can be imparted by, for example, enhancing dihydrodipicolinate synthase activity and/or aspartokinase activity.

The dihydrodipicolinate synthase activity and/or the aspartokinase activity in *Methylophilus* bacteria can be enhanced by ligating a gene fragment coding for dihydrodipicolinate synthase and/or a gene fragment coding for aspartokinase with a vector that functions in *Methylophilus* bacteria, preferably a multiple copy type vector, to create a recombinant DNA, and introducing them into a *Methylophilus* bacterium host to transform the host. As a result of the increase in the copy numbers of the gene coding for dihydrodipicolinate synthase and/or the gene coding for aspartokinase in cells of the transformant strain, the activity or activities thereof is/are enhanced. Hereafter, dihydrodipicolinate synthase, aspartokinase and aspartokinase III are also referred with abbreviations of DDPS, AK and AKIII, respectively.

As a microorganism providing a gene that codes for DDPS and a gene that codes for AK, any microorganisms can be used so long as they have genes enabling expression of DDPS activity and AK activity in microorganisms belonging to the genus *Methylophilus*. Such microorganisms may be wild strains or mutant strains derived therefrom. Specifically, examples of such microorganisms include *E. coli* (*Escherichia coli*) K-12 strain, *Methylophilus methylotrophus* AS1 strain (NCIMB10515) and so forth. Since nucleotide sequences of a gene coding for DDPS (dapA, Richaud, F. et al., J. Bacteriol., 297, (1986)) and a gene coding for AKIII (lysC, Cassan, M., Parsot, C., Cohen, G. N. and Patte, J. C., J. Biol. Chem., 261, 1052 (1986)) derived from *Escherichia* bacteria have been both revealed, these genes can be obtained by PCR using primers synthesized based on the nucleotide sequences of these genes and chromosome DNA of microorganism such as *E. coli* K-12 or the like as a template. As specific examples, dapA and lysC derived from *E. coli* will be explained below. However, genes used for the present invention are not limited to them.

It is preferred that DDPS and AK used for the present invention do not suffer feedback inhibition by L-lysine. It has been known that wild-type DDPS derived from *E. coli* suffers feedback inhibition by L-lysine, and that wild-type AKIII derived from *E. coli* suffers suppression and feedback inhibition by L-lysine. Therefore, dapA and lysc to be introduced into *Methylophilus* bacteria preferably code for DDPS and AKIII having a mutation that desensitizes the feedback inhibition by L-lysine. Hereafter, DDPS having a mutation that desensitizes the feedback inhibition by L-lysine is also referred to as "mutant DDPS", and DNA coding for the mutant DDPS is also referred to as "mutant dapA". AKIII derived from *E. coli* having a mutation that desensitizes the feedback inhibition by L-lysine is also referred to as "mutant AKIII", and DNA coding for the mutant AKIII is also referred to as "mutant lysC".

According to the present invention, DDPS and AK are not necessarily required to be a mutant. It has been known that, for example, DDPS derived from *Corynebacterium* bacteria originally does not suffer feedback inhibition by L-lysine.

A nucleotide sequence of wild-type dapA derived from *E. coli* is exemplified by SEQ ID NO: 1. The amino acid sequence of wild-type DDPS coded by said nucleotide sequence is exemplified by SEQ ID NO: 2. A nucleotide sequence of wild-type lysC derived from *E. coli* is exemplified by SEQ ID NO: 3. The amino acid sequence of wild-type ATIII coded by said nucleotide sequence is exemplified by SEQ ID NO: 4.

The DNA coding for mutant DDPS that does not suffer feedback inhibition by L-lysine includes a DNA coding for DDPS having the amino acid sequence described in SEQ ID NO: 2 wherein the 118-histidine residue is replaced with a tyrosine residue. The DNA coding for mutant AKIII that does not suffer feedback inhibition by L-lysine includes a DNA coding for AKIII having an amino sequence described in SEQ ID NO: 4 wherein the 352-threonine residue is replaced with an isoleucine residue.

The plasmid used for gene cloning may be any plasmid so long as it can replicate in microorganisms such as *Escherichia* bacteria or the like, and specifically include pBR322, pTWV228, pMW119, pUC19 and so forth.

The vector that functions in *Methylophilus* bacteria is, for example, a plasmid that can autonomously replicate in *Methylophilus* bacteria. Specifically, there can be mentioned RSF1010, which is a broad host spectrum vector, and derivatives thereof, for example, pAYC32 (Chistorerdov, A. Y., Tsygankov, Y. D. Plasmid, 16, 161–167, (1986)), pMFY42 (Gene, 44, 53, (1990)), pRP301, pTB70 (Nature, 287, 396, (1980)) and so forth.

In order to prepare a recombinant DNA by ligating dapA and lysC to a vector that functions in *Methylophilus* bacteria, the vector is digested with a restriction enzyme that corresponds to the terminus of DNA fragment containing dapA and lysc. Ligation is usually performed by using ligase such as T4 DNA ligase. dapA and lysC may be individually incorporated into separate vectors or into a single vector.

As a plasmid containing a mutant dapA coding for mutant DDPS and a mutant lysC coding for mutant AKIII, a broad host spectrum plasmid RSFD80 has been known (WO95/16042). *E. coli* JM109 strain transformed with this plasmid was designated as AJ12396, and deposited at National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Oct. 28, 1993 and received an accession number of FERM P-13936, and it was transferred to an international deposition under the provisions of the Budapest Treaty on Nov. 1, 1994, and received an accession number of FERM BP-4859. RSFD80 can be obtained from the AJ12396 strain in a known manner.

The mutant dapA contained in RSFD80 has a nucleotide sequence of wild-type dapA of SEQ ID NO: 1 including replacement of C at the nucleotide number 623 with T. The mutant DDPS encoded thereby has an amino acid sequence of SEQ ID NO: 2 including replacement of the 118-histidine residue with a tyrosine residue. The mutant lysC contained in RSFD80 has a nucleotide sequence of wild-type lysC of SEQ ID NO: 3 including replacement of C at the nucleotide number 1638 with T. The mutant AKIII encoded thereby has an amino acid sequence of SEQ ID NO: 4 including replacement of the 352-threonine residue with an isoleucine residue.

In order to introduce a recombinant DNA prepared as described above into *Methylophilus* bacteria, any method can be used so long as it provides sufficient transformation efficiency. For example, electroporation can be used (Canadian Journal of Microbiology, 43, 197 (1997)).

The DDPS activity and/or the AK activity can also be enhanced by the presence of multiple copies of dapA and/or lysC on chromosome DNA of *Methylophilus* bacteria. In order to introduce multiple copies of dapA and/or lysC into chromosome DNA of *Methylophilus* bacteria, homologous recombination is performed by using, as a target, a sequence that is present on chromosome DNA of *Methylophilus* bacteria in a multiple copy number. As the sequence present on chromosome DNA in the multiple copy number, a repetitive DNA, inverted repeats present at the end of a transposable element, or the like can be used. Alternatively, as disclosed in Japanese Patent Application Laid-open (Kokai) No. 2-109985/1990, multiple copies of dapA and/or lysC can be introduced into chromosome DNA by mounting them on a transposon to transfer them. In both of the methods, as a result of increased copy number of dapA and/or lysC in transformed strains, the DDPS activity and the AK activity should be amplified.

Besides the above gene amplification, the DDPS activity and/or the AK activity can be amplified by replacing an expression control sequence such as promoters of dapA and/or lysc with stronger ones (Japanese Patent Application Laid-open (Kokai) No. 1-4 215280/1989). As such strong promoters, there have been known, for example, lac promoter, trp promoter, trc promoter, tac promoter, $P_R$ promoter and $P_L$ promoter of lambda phage, tet promoter, amyE promoter, spac promoter and so forth. Substitution of these promoters enhances expression of dapA and/or lysC, and thus the DDPS activity and the AK activity are amplified.

Enhancement of expression control sequences can be combined with increase of the copy numbers of dapA and/or lysc.

In order to prepare a recombinant DNA by ligating a gene fragment and a vector, the vector is digested with a restriction enzyme corresponding to the terminus of the gene fragment. Ligation is usually performed by ligase such as T4 DNA ligase. As methods for digestion, ligation and others of DNA, preparation of chromosome DNA, PCR, preparation of plasmid DNA, transformation, design of oligonucleotides used as primers and so forth, usual methods well known to those skilled in the art can be used. Such methods are described in Sambrook, J., Fritsch, E. F., and Maniatis, T., "Molecular Cloning: A Laboratory Manual, 2nd Edition", Cold Spring Harbor Laboratory Press, (1989) and so forth.

In addition to the enhancement of the DDPS activity and/or the AK activity, activity of another enzyme involved in the L-lysine biosynthesis may also be enhanced. Such enzymes include diaminopimelate pathway enzymes such as dihydrodipicolinate reductase, diaminopimelate decarboxylase, diaminopimelate dehydrogenase (WO96/40934 for all of the foregoing enzymes), phosphoenolpyruvate carboxylase (Japanese Patent Application Laid-open (Kokai) No. 60-87788/1985), aspartate aminotransferase (Japanese Patent Publication (Kokoku) No. 6-102028/1994), diaminopimelate epimerase, aspartic acid semialdehyde dehydrogenase and so forth, or aminoadipate pathway enzymes such as homoaconitate hydratase and so forth. Preferably, activity of at least one enzyme of aspartic acid semialdehyde dehydrogenase, dihydrodipicolinate reductase and diaminopimelate decarboxylase is enhanced.

Aspartokinase, aspartic acid semialdehyde dehydrogenase, dihydrodipicolinate synthase, dihydrodipicolinate reductase and diaminopimelate decarboxylase derived form *Methylophilus methylotrophus* will be described later.

Further, the microorganisms of the present invention may be decreased in activity of an enzyme that catalyzes a reaction for generating a compound other than L-lysine by branching off from the biosynthetic pathway of L-lysine, or may be deficient in such an enzyme. The enzyme that catalyzes the reaction for generating the compound other than L-lysine by branching off from the biosynthetic pathway L-lysine include homoserine dehydrogenase (see WO95/23864).

The aforementioned techniques for enhancing activity of an enzyme involved in the L-lysine biosynthesis can be similarly used for other amino acids mentioned below.

[L-Glutamic Acid]

L-Glutamic acid-producing ability can be imparted to *Methylophilus* bacteria by, for example, introducing a DNA that codes for any one of enzymes including glutamate dehydrogenase (Japanese Patent Application Laid-open (Kokai) 61-268185/1986), glutamine synthetase, glutamate synthase, isocitrate dehydrogenase (Japanese Patent Application Laid-open (Kokai) Nos. 62-166890/1987 and 63-214189/1988), aconitate hydratase (Japanese Patent Application Laid-open (Kokai) No. 62-294086/1987), citrate synthase (Japanese Patent Application Laid-open (Kokai) Nos. 62-201585/1987 and 63-119688/1988), phosphoenolpyruvate carboxylase (Japanese Patent Application Laid-open (Kokai) Nos. 60-87788/1985 and 62-55089/1987), pyruvate dehydrogenase, pyruvate kinase, phosphoenolpyruvate synthase, enolase, phosphoglyceromutase, phosphoglycerate kinase, glyceraldehyde-3-phosphate dehydrogenase, triose phosphate isomerase, fructose bisphosphate aldolase, phosphofructokinase (Japanese Patent Application Laid-open (Kokai) No. 63-102692/1988), glucose phosphate isomerase, glutamine-oxoglutarate aminotransferase (WO99/07853) and so forth.

Further, the microorganisms of the present invention may be decreased in activity of an enzyme that catalyzes a reaction for generating a compound other than L-glutamic acid by branching off from the biosynthetic pathway of L-glutamic acid, or may be deficient in such an enzyme. The enzyme that catalyzes the reaction for generating the compound other than L-glutamic acid by branching off from the biosynthetic pathway L-glutamic acid include α-ketoglutarate dehydrogenase (αKGDH), isocitrate lyase, phosphate acetyltransferase, acetate kinase, acetohydroxy acid synthase, acetolactate synthase, formate acetyltransferase, lactate dehydrogenase, glutamate decarboxylase, 1-pyrroline dehydrogenase and so forth.

[L-Threonine]

L-Threonine-producing ability can be imparted or enhanced by, for example, enhancing activities of aspartokinase, homoserine dehydrogenase, homoserine kinase and threonine synthase. The activities of these enzymes can be enhanced by, for example, transforming *Methylophilus* bacteria using a recombinant plasmid containing a threonine operon (Japanese Patent Application Laid-open (Kokai) Nos. 55-131397/1980, 59-31691/1984 and 56-15696/1981 and Japanese Patent Application Laid-open (Kohyo) No. 3-501682/1991).

The production ability can also be imparted or enhanced by amplifying or introducing a threonine operon having a gene coding for aspartokinase of which feedback inhibition by L-threonine is desensitized (Japanese Patent Publication (Kokoku) No. 1-29559/1989), a gene coding for homoserine dehydrogenase (Japanese Patent Application Laid-open (Kokai) No. 60-012995/1985) or a gene coding for homoserine kinase and homoserine dehydrogenase (Japanese Patent Application Laid-open (Kokai) No. 61-195695/1986).

Further, L-threonine-producing ability can be improved by introducing a DNA coding for a mutant phosphoenolpyruvate carboxylase having a mutation for desensitizing feedback inhibition by aspartic acid.

[L-Valine]

L-Valine-producing ability can be imparted by, for example, introducing into *Methylophilus* bacteria an L-valine biosynthesis gene whose control mechanism has been substantially desensitized. There may also be introduced a mutation that substantially desensitizes a control mechanism of an L-valine biosynthesis gene carried by a microorganism belonging to the genus *Methylophilus*.

Examples of the L-valine biosynthesis gene include, for example, the ilvGMEDA operon of *E. coli*. Threonine deaminase encoded by an ilvA gene catalyzes the deamination reaction converting L-threonine into 2-ketobutyric acid, which is the rate-determining step of L-isoleucine biosynthesis. Therefore, in order to attain efficient progression of the L-valine synthesis reactions, it is preferable to use an operon that does not express threonine deaminase activity. Examples of the ilvGMEDA operon that does not express such threonine deaminase activity include an ilvGMEDA operon wherein a mutation for eliminating threonine deaminase activity is introduced into ilvA, or ilvA is disrupted, and an ilvGMED operon wherein ilvA is deleted.

Since the ilvGMEDA operon suffers expression control of operon (attenuation) by L-valine and/or L-isoleucine and/or L-leucine, the region required for the attenuation is preferably removed or mutated to desensitize the suppression of expression by L-valine.

An ilvGMEDA operon which does not express threonine deaminase activity and in which attenuation is desensitized as described above can be obtained by subjecting a wild-type ilvGMEDA operon to a mutagenesis treatment or modifying it by means of gene recombination techniques (see WO96/06926).

[L-Leucine]

L-Leucine-producing ability is imparted or enhanced by, for example, introducing into a microorganism belonging to the genus *Methylophilus* an L-leucine biosynthesis gene whose control mechanism has been substantially desensitized, in addition to the above characteristics required for the production of L-valine. It is also possible to introduce such a mutation that the control mechanism of an L-leucine biosynthesis gene in a microorganism belonging to the genus *Methylophilus* should be substantially eliminated. Examples of such a gene include, for example, an leuA gene which provides an enzyme in which inhibition by L-leucine is substantially eliminated.

[L-Isoleucine]

L-Isoleucine-producing ability can be imparted by, for example, introducing a thrABC operon containing a thrA gene coding for aspartokinase I/homoserine dehydrogenase I derived from *E. coli* wherein inhibition by L-threonine has been substantially desensitized and an ilvGMEDA operon which contains an ilvA gene coding for threonine deaminase wherein inhibition by L-isoleucine is substantially desensitized and whose region required for attenuation is removed (Japanese Patent Application Laid-open (Kokai) No. 8-47397/1996).

[Other Amino Acids]

Biosyntheses of L-tryptophan, L-phenylalanine, L-tyrosine, L-threonine and L-isoleucine can be enhanced by increasing phosphoenolpyruvate-producing ability of *Methylophilus* bacteria (WO97/08333).

The production abilities for L-phenylalanine and L-tyrosine are improved by amplifying or introducing a desensitized chorismate mutase-prephenate dehydratase (CM-PDT) gene (Japanese Patent Application Laid-open (Kokai) Nos. 5-236947/1993 and 62-130693/1987) and a desensitized 3-deoxy-D-arabinoheptulonate-7-phosphate synthase (DS) gene (Japanese Patent Application Laid-open (Kokai) Nos. 5-236947/1993 and 61-124375/1986).

The producing ability of L-tryptophan is improved by amplifying or introducing a tryptophan operon containing a gene coding for desensitized anthranilate synthase (Japanese Patent Application Laid-open (Kokai) Nos. 57-71397/1982, 62-244382/1987 and U.S. Pat. No. 4,371,614).

In the present specification, the expression that enzyme "activity is enhanced" usually refers to that the intracellular activity of the enzyme is higher than that of a wild type strain, and when a strain in which the activity of the enzyme is enhanced is obtained by modification using gene recombinant techniques or the like, the intracellular activity of the enzyme is higher than that of the strain before the modification. The expression that enzyme "activity is decreased" usually refers to that the intracellular activity of the enzyme is lower than that of a wild type strain, and when a strain in which the activity of the enzyme is decreased is obtained by modification using gene recombinant techniques or the like, the intracellular activity of the enzyme is lower than that of the strain before the modification.

L-Amino acids can be produced by culturing *Methylophilus* bacteria having L-amino acid-producing ability obtained as described above in a medium to produce and accumulate L-amino acids in the culture, and collecting the L-amino acids from the culture.

Bacterial cells of *Methylophilus* bacteria with an increased L-amino acid content compared with wild strains of *Methylophilus* bacteria can be produced by culturing *Methylophilus* bacteria having L-amino acid-producing ability in a medium to produce and accumulate L-amino acids in bacterial cells of the bacteria.

Microorganisms used for the present invention can be cultured by methods usually used for culturing microorganisms having methanol-assimilating property. The medium used for the present invention may be a natural or synthetic medium so long as it contains a carbon source, a nitrogen source, inorganic ions and other trace amount organic constituents as required.

By using methanol as a main carbon source, L-amino acids can be prepared at a low cost. When methanol is used as a main carbon source, it is usually added to a medium in an amount of 0.001 to 30%. As the nitrogen source, ammonium sulfate or the like is used by adding it to the medium. Other than these, there are usually added small amounts of the trace amount constituents such as potassium phosphate, sodium phosphate, magnesium sulfate, ferrous sulfate and manganese sulfate.

The culture is usually performed under an aerobic condition obtained by, for example, shaking or stirring for aeration, at pH 5 to 9 and a temperature of 20 to 45° C., and it is usually completed within 24 to 120 hours.

Collection of L-amino acids from culture can be usually attained by a combination of known methods such as those using ion exchange resin, precipitation and others.

Further, *Methylophilus* bacterium cells can be separated from the medium by usual methods for separating microbial cells.

<2> Gene of the Present Invention

The DNA of the present invention is a gene which codes for one of the enzymes, aspartokinase (henceforth also abbreviated as "AK"), aspartic acid semialdehyde dehydrogenase (henceforth also abbreviated as "ASD"), dihydrodipicolinate synthase (henceforth also abbreviated as "DDPS"), dihydrodipicolinate reductase (henceforth also abbreviated as "DDPR"), and diaminopimelate decarboxylase (henceforth also abbreviated as "DPDC") derived from *Methylophilus methylotrophus.*

The DNA of the present invention can be obtained by, for example, transforming a mutant strain of a microorganism deficient in AK, ASD, DDPS, DDPR or DPDC using a gene library of *Methylophilus methylotrophus*, and selecting a clone in which auxotrophy is recovered.

A gene library of *Methylophilus methylotrophus* can be produced as follows, for example. First, total chromosome DNA is prepared from a *Methylophilus methylotrophus* wild strain, for example, the *Methylophilus methylotrophus* AS1 strain (NCIMB10515), by the method of Saito et al. (Saito, H. and Miura, K., Biochem. Biophys. Acta 72, 619–629, (1963)) or the like, and partially digested with a suitable restriction enzyme, for example, Sau3AI or AluI, to obtain a mixture of various fragments. By controlling the degree of the digestion through adjustment of digestion reaction time and so forth, a wide range of restriction enzymes can be used.

Subsequently, the digested chromosome DNA fragments are ligated to vector DNA autonomously replicable in

*Escherichia coli* cells to produce recombinant DNA. Specifically, a restriction enzyme producing the same terminal nucleotide sequence as that produced by the restriction enzyme used for the digestion of chromosome DNA is allowed to act on the vector DNA to fully digest and cleave the vector. Then, the mixture of chromosome DNA fragments and the digested and cleaved vector DNA are mixed, and a ligase, preferably T4 DNA ligase, is allowed to act on the mixture to obtain recombinant DNA.

A gene library solution can be obtained by transforming *Escherichia coli*, for example, the *Escherichia coli* JM109 strain or the like, using the obtained recombinant DNA, and preparing recombinant DNA from the culture broth of the transformant. This transformation can be performed by the method of D. M. Morrison (Methods in Enzymology 68, 326 (1979)), the method of treating recipient cells with calcium chloride so as to increase the permeability of DNA (Mandel, M. and Higa, A., J. Mol. Biol., 53, 159 (1970)) and so forth. In the examples mentioned hereinafter, electroporation was used.

As examples of the aforementioned vector, there can be mentioned pUC19, pUC18, pUC118, pUC119, pBR322, pHSG299, pHSG298, pHSG399, pHSG398, RSF1010, pMW119, pMW118, pMW219, pMW218, pSTV28, pSTV29 and so forth. Phage vectors can also be used. Since pUC118 and pUC119 contain an ampicillin resistance gene, and pSTV28 and pSTV29 contain a chloramphenicol resistance gene, for example, only transformants which harbor a vector or a recombinant DNA can be grown by using a medium containing ampicillin or chloramphenicol.

As the method for culturing the transformants and collecting recombinant DNA from bacterial cells, the alkali SDS method and the like can be mentioned.

A mutant microbial strain deficient in AK, ASD, DDPS, DDPR or DPDC is transformed by using the gene library solution of *Methylophilus methylotrophus* obtained as described above, and clones whose auxotrophy is recovered are selected.

Examples of a mutant microbial strain deficient in AK include *E. coli* GT3 deficient in three kinds of genes coding for AK (thrA, metLM, lysC). Examples of a mutant microbial strain deficient in ASD include *E. coli* Hfr3000 U482 (CGSC 5081 strain). Examples of a mutant microbial strain deficient in DDPS include *E. coli* AT997 (CGSC 4547 strain). Examples of a mutant microbial strain deficient in DDPR include *E. coli* AT999 (CGSC 4549 strain). Examples of a mutant microbial strain deficient in DPDC include *E. coli* AT2453 (CGSC 4505 strain). These mutant strains can be obtained from *E. coli* Genetic Stock Center (the Yale University, Department of Biology, Osborn Memorial Labs., P.O. Box 6666, New Haven 06511-7444, Conn., U.S.).

Although all of the aforementioned mutant strains cannot grow in M9 minimal medium, transformant strains which contain a gene coding for AK, ASD, DDPS, DDPR or DPDC can grow in M9 minimal medium because these genes function in the transformants. Therefore, by selecting transformant strains that can grow in the minimal medium and collecting recombinant DNA from the strains, DNA fragments containing a gene that codes for each enzyme can be obtained. *E. coli* AT999 (CGSC 4549 strain) shows extremely slow growth rate even in a complete medium such as L medium when diaminopimelic acid is not added to the medium. However, normal growth can be observed for its transformant strains which contain a gene coding for DDPR derived from *Methylophilus methylotrophus*, because of the function of the gene. Therefore, a transformant strain that contains a gene coding for DDPR can also be obtained by selecting a transformant strain normally grown in L medium.

By extracting an insert DNA fragment from the obtained recombinant DNA and determining its nucleotide sequence, an amino acid sequence of each enzyme and nucleotide sequence of the gene coding for it can be determined.

The gene coding for AK of the present invention (henceforth also referred to "ask") codes for AK which has the amino acid sequence of SEQ ID NO: 6 shown in Sequence Listing. As a specific example of the ask gene, there can be mentioned a DNA having the nucleotide sequence which consists of nucleotides of SEQ ID NO: 5. The ask gene of the present invention may have a sequence in which codon corresponding to each of the amino acids is replaced with equivalent codon so long as it codes for the same amino acid sequence as the amino acid sequence of SEQ ID NO: 6.

The gene which codes for ASD of the present invention (henceforth also referred to as "asd") codes for ASD which has the amino acid sequence of SEQ ID NO: 8 shown in Sequence Listing. As a specific example of the asd gene, a DNA which contains the nucleotide sequence consisting of the nucleotides of the nucleotide numbers 98–1207 in SEQ ID NO: 7 can be mentioned. The asd gene of the present invention may have a sequence in which codon corresponding to each of the amino acids is replaced with equivalent codon so long as it codes for the same amino acid sequence as the amino acid sequence of SEQ ID NO: 8.

The gene which codes for DDPS of the present invention (henceforth also referred to as "dapA") codes for DDPS which has the amino acid sequence of SEQ ID NO: 10 shown in Sequence Listing. As a specific example of the dapA gene, a DNA which has the nucleotide sequence consisting of the nucleotides of the nucleotide numbers 1268–2155 in SEQ ID NO: 9 can be mentioned. The dapA gene of the present invention may have a sequence in which codon corresponding to each of the amino acids is replaced with equivalent codon so long as it codes for the same amino acid sequence as the amino acid sequence of SEQ ID NO: 10.

The gene which codes for DDPR of the present invention (henceforth also referred to as "dapB") codes for DDPR which has the amino acid sequence of SEQ ID NO: 12 shown in Sequence Listing. As a specific example of the dapB gene, a DNA which has the nucleotide sequence consisting of the nucleotides of the nucleotide numbers 2080–2883 in SEQ ID NO: 11 can be mentioned. The dapB gene of the present invention may have a sequence in which codon corresponding to each of the amino acids is replaced with equivalent codon so long as it codes for the same amino acid sequence as the amino acid sequence of SEQ ID NO: 12.

The gene which codes for DPDC of the present invention (henceforth also referred to as "lysA") codes for DPDC which has the amino acid sequence of SEQ ID NO: 14 shown in Sequence Listing. As a specific example of the lysA gene, a DNA which has the nucleotide sequence consisting of the nucleotides of the nucleotide numbers 751–1995 in SEQ ID NO: 13 can be mentioned. The lysA gene of the present invention may have a sequence in which codon corresponding to each of the amino acids is replaced with equivalent codon so long as it codes for the same amino acid sequence as the amino acid sequence of SEQ ID NO: 14.

The gene for each enzyme of the present invention may have an amino acid sequence corresponding to each amino acid sequence of SEQ ID NO: 6, 8, 10, 12 or 14 including substitution, deletion, insertion, addition or inversion of one or several amino acids, and may code a protein having activity of AK, ASD, DDPS, DDPR or DPDC. The expression "one or several" used herein preferably means a number of 1 to 10, more preferably a number of 1 to 5, more preferably a number of 1 to 2.

The DNA which codes for the substantially same protein as AK, ASD, DDPS, DDPR or DPDC such as those mentioned above can be obtained by modifying each nucleotide sequence so that the amino acid sequence should contain substitution, deletion, insertion, addition or inversion of an amino acid residue or residues at a particular site by, for example, site-specific mutagenesis. Such a modified DNA as mentioned above may also be obtained by a conventional mutagenesis treatment. Examples of the mutagenesis treatment include in vitro treatment of DNA coding for AK, ASD, DDPS, DDPR or DPDC with hydroxylamine or the like, treatment of a microorganism such as *Escherichia* bacteria containing a gene coding for AK, ASD, DDPS, DDPR or DPDC by UV irradiation or with mutagenesis agents used for usual mutagenesis treatment such as N-methyl-N'-nitro-N-nitrosoguanidine (NTG) and nitrous acid.

The aforementioned substitution, deletion, insertion, addition or inversion of nucleotides includes naturally occurring mutations (mutant or variant) such as those observed depending difference between species or strains of microorganisms containing AK, ASD, DDPS, DDPR or DPDC and so forth.

The DNA which codes for substantially the same protein as AK, ASD, DDPS, DDPR or DPDC can be obtained by allowing expression of a DNA having such a mutation as mentioned above in a suitable cell, and examining AK, ASD, DDPS, DDPR or DPDC activity of the expression product. The DNA which codes for substantially the same protein as AK, ASD, DDPS, DDPR or DPDC can also be obtained by isolating, from DNAs coding for AK, ASD, DDPS, DDPR or DPDC which have mutations or cells containing each of them, a DNA hybridizable with a probe containing a nucleotide sequence comprising the nucleotide sequence of the nucleotide numbers 510–1736 of SEQ ID NO: 5, a nucleotide sequence comprising the nucleotide sequence of the nucleotide numbers 98–1207 of SEQ ID NO: 7, a nucleotide sequence comprising the nucleotide sequence of the nucleotide numbers 1268–2155 of SEQ ID NO: 9, a nucleotide sequence comprising the nucleotide sequence of the nucleotide numbers 2080–2883 of SEQ ID NO: 11, or a nucleotide sequence comprising the nucleotide sequence of the nucleotide numbers 751–1995 of SEQ ID NO: 13, or a part of those nucleotide sequences under a stringent condition, and coding for a protein having AK, ASD, DDPS, DDPR or DPDC activity. In the present specification, to have a nucleotide sequence or a part thereof means to have the nucleotide sequence or the part thereof, or a nucleotide complementary thereto.

The term "stringent condition" used herein means a condition that allows formation of so-called specific hybrid and does not allow formation of non-specific hybrid. This condition may vary depending on the nucleotide sequence and length of the probe. However, it may be, for example, a condition that allows hybridization of highly homologous DNA such as DNA having homology of 40% or higher, but does not allow hybridization of DNA of lower homology than defined above, or a condition that allows hybridization under a washing condition of usual Southern hybridization, of a temperature of 60° C. and salt concentrations corresponding to 1×SSC and 0.1% SDS, preferably 0.1×SSC and 0.1% SDS.

A partial sequence of each gene can also be used as the probe. Such a probe can be produced by PCR (polymerase chain reaction) using oligonucleotides produced based on a nucleotide sequence of each gene as primers and a DNA fragment containing each gene as a template. When a DNA fragment having a length of about 300 bp is used as the probe, washing condition for hybridization may be, for example, 50° C., 2×SSC and 0.1% SDS.

Genes that hybridize under such a condition as mentioned above also include those having a stop codon occurring in its sequence and those encoding an enzyme no longer having its activity due to a mutation of active center. However, such genes can readily be eliminated by ligating the genes to a commercially available activity expression vector, and measuring AK, ASD, DDPS, DDPR or DPDC activity.

Since the nucleotide sequences of the genes that codes for AK, ASD, DDPS, DDPR and DPDC derived from *Methylophilus methylotrophus* were revealed by the present invention, DNA sequences which code for AK, ASD, DDPS, DDPR and DPDC can be obtained from a *Methylophilus methylotrophus* gene library by hybridization using oligonucleotide probes produced based on the sequences. Moreover, DNA sequences which code for these enzymes can also be obtained by amplifying them from *Methylophilus methylotrophus* chromosome DNA by PCR using oligonucleotide primers produced based on the aforementioned nucleotide sequences.

The aforementioned genes can suitably be utilized to enhance L-lysine-producing ability of *Methylophilus* bacteria.

EXAMPLES

The present invention will further specifically be explained with reference to the following examples hereafter.

The reagents used were obtained from Wako Pure Chemicals or Nakarai Tesque unless otherwise indicated. The compositions of the media used in each example are shown below. pH was adjusted with NaOH or HCl for all media.

| (L medium) | |
|---|---|
| Bacto trypton (DIFCO) | 10 g/L |
| Yeast extract (DIFCO) | 5 g/L |
| NaCl | 5 g/L |

[steam-sterilized at 120° C. for 20 minutes]

| (L agar medium) | |
|---|---|
| L medium | |
| Bacto agar (DIFCO) | 15 g/L |

[steam-sterilized at 120° C. for 20 minutes]

| (SOC medium) | |
|---|---|
| Bacto trypton (DIFCO) | 20 g/L |
| Yeast extract (DTFCO) | 5 g/L |
| 10 mM | NaCl |
| 2.5 mM | KCl |
| 10 mM | $MgSO_4$ |

-continued

| (SOC medium) | |
|---|---|
| 10 mM | $MgCl_2$ |
| 20 mM | Glucose |

[The constituents except for magnesium solution and glucose were steam-sterilized (120° C., 20 minutes), then 2 M magnesium stock solution (1 M $MgSO_4$, 1 M $MgCl_2$) and 2 M glucose solution, which solutions had been passed through a 0.22-μm filter, were added thereto, and the mixture was passed through a 0.22-μm filter again.]

| (121M1 medium) | |
|---|---|
| $K_2HPO_4$ | 1.2 g/L |
| $KH_2PO_4$ | 0.62 g/L |
| NaCl | 0.1 g/L |
| $(NH_4)_2SO_4$ | 0.5 g/L |
| $MgSO_4 \cdot 7H_2O$ | 0.2 g/L |
| $CaCl_2 \cdot 6H_2O$ | 0.05 g/L |
| $FeCl_3 \cdot 6H_2O$ | 1.0 mg/L |
| $H_3BO_3$ | 10 μg/L |
| $CuSO_4 \cdot 5H_2O$ | 5 μg/L |
| $MnSO_4 \cdot 5H_2O$ | 10 μg/L |
| $ZnSO_4 \cdot 7H_2O$ | 70 μg/L |
| $NaMoO_4 \cdot 2H_2O$ | 10 μg/L |
| $CoCl_2 \cdot 6H_2O$ | 5 μg/L |
| Methanol 1% (vol/vol), | pH 7.0 |

[The constituents except for methanol were steam-sterilized at 121° C. for 15 minutes. After the constituents sufficiently cooled, methanol was added.]

| (Composition of 121 production medium) | |
|---|---|
| Methanol | 2% |
| Dipotassium phosphate | 0.12% |
| Potassium phosphate | 0.062% |
| Calcium chloride hexahydrate | 0.005% |
| Magnesium sulfate heptahydrate | 0.02% |
| Sodium chloride | 0.01% |
| Ferric chloride hexahydrate | 1.0 mg/L |
| Ammonium sulfate | 0.3% |
| Cupric sulfate pentahydrate | 5 μg/L |
| Manganous sulfate pentahydrate | 10 μg/L |
| Sodium molybdate dihydrate | 10 μg/L |
| Boric acid | 10 μg/L |
| Zinc sulfate heptahydrate | 70 μg/L |
| Cobaltous chloride hexahydrate | 5 μg/L |
| Calcium carbonate (Kanto Kagaku) | 3% |
| (pH 7.0) | |

| (121M1 Agar medium) | |
|---|---|
| 121M1 medium | |
| Bacto agar (DIFCO) | 15 g/L |

[The constituents except for methanol were steam-sterilized at 121° C. for 15 minutes. After the constituents sufficiently cooled, methanol was added.]

| (M9 minimal medium) | |
|---|---|
| $Na_2HPO_4 \cdot 12H_2O$ | 16 g/L |
| $KH_2PO_4$ | 3 g/L |
| NaCl | 0.5 g/L |
| $NH_4Cl$ | 1 g/L |
| $MgSO_4 \cdot 7H_2O$ | 246.48 mg/L |
| Glucose | 2 g/L |
| pH 7.0 | |

[$MgSO_4$ and glucose were separately sterilized (120° C., 20 minutes) and added. A suitable amount of amino acids and vitamins were added as required.]

| (M9 minimal agar medium) | |
|---|---|
| M9 minimal medium | |
| Bacto agar (DIFCO) | 15 g/L |

Example 1

Creation of L-Lysine-Producing Bacterium (1)

(1) Introduction of Mutant lysC and Mutant dapA into *Methylophilus* Bacterium

A mutant lysC and a mutant dapA were introduced into a *Methylophilus* bacterium by using a known plasmid RSFD80 (see WO95/16042) containing them. RSFD80 is a plasmid pVIC40 (International Publication WO90/04636, Japanese Patent Application Laid-open (Kohyo) No. 3-501682/1991) derived from a broad host spectrum vector plasmid pAYC32 (Chistorerdov, A. Y., Tsygankov, Y. D., Plasmid, 16, 161–167, (1986)), which is a derivative of RSF1010, in which a mutant dapA and a mutant lysc derived from *E. coli* are located in this order downstream of the promoter (tetP) of the tetracycline resistance gene of pVIC40 so that the transcription directions of the genes are ordinary with respect to tetP. The mutant dapA coded for a mutant DDPS in which the 118-histidine residue was replaced with a thyrosine residue. The mutant lysC coded for a mutant AKIII in which the 352-threonine residue was replaced with an isoleucine residue.

Figure 2:
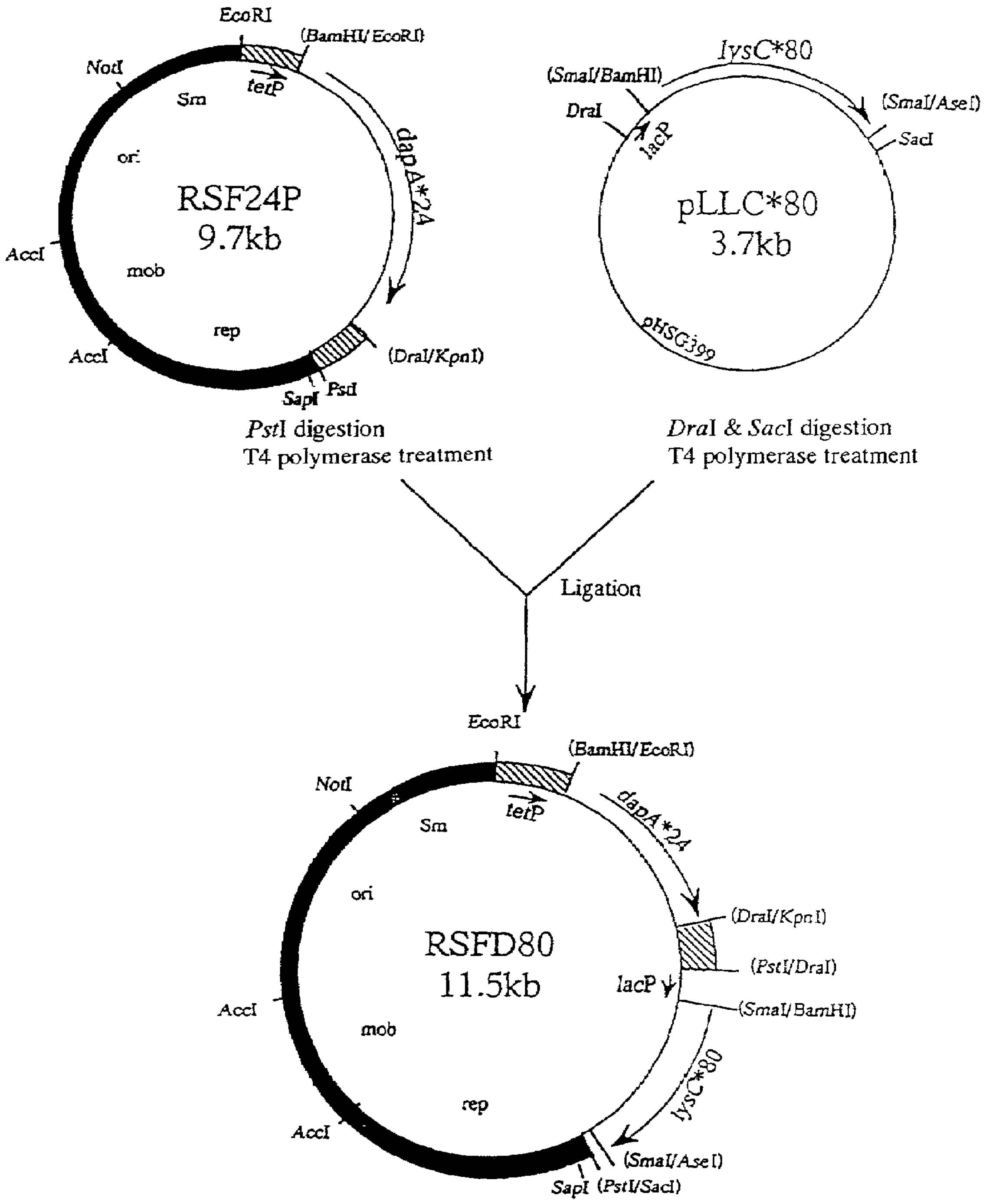
FIG. 2 shows the production process of plasmid RSFD80 having a mutant dapA and a mutant lysC. The "lysC*80" refers to a mutant lysC that codes for a mutant AKIII wherein the 352-threonine residue is replaced with an isoleucine residue.

RSFD80 was constructed as follows. The mutant dapA on a plasmid pdapAS24 was ligated to pVIC40 at a position downstream of the promoter of the tetracycline resistance gene to obtain RSF24P as shown in FIG. 1. Then, the plasmid RSFD80 which had the mutant dapA and a mutant lysc was prepared from RSF24P and pLLC*80 containing the mutant lysC as shown in FIG. 2. That is, while pVIC40 contains a threonine operon, this threonine operon is replaced with a DNA fragment containing the mutant dapA and a DNA fragment containing the mutant lysC in RSFD80.

The *E. coli* JM109 strain transformed with the RSFD80 plasmid was designated as AJ12396, and deposited at National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Oct. 28, 1993 and received an accession number of FERM P-13936, and it was transferred to an international deposition under the provisions of the Budapest Treaty on Nov. 1, 1994, and received an accession number of FERM BP-4859.

The *E. coli* AJ1239 strain was cultured in 30 ml of LB medium containing 20 mg/L of streptomycin at 30° C. for 12 hours, and the RSFD80 plasmid was purified from the obtained cells by using Wizard® Plus Midipreps DNA Purification System (sold by Promega).

The RSFD80 plasmid produced as described above was introduced into the *Methylophilus methylotrophus* AS1 strain (NCIMB10515) by electroporation (Canadian Journal of Microbiology, 43, 197 (1997)). As a control, a DNA region coding for the threonine operon was deleted from the pVIC40 plasmid used for producing the RSFD80 plasmid to produce a pRS plasmid comprising only the vector region (see Japanese Patent Application Laid-open (Kohyo) No. 3-501682/1991), and the pRS plasmid was introduced into the AS1 strain in the same manner as that used for RSFD80.

(2) AKIII Activity of *Methylophilus* Bacterium Containing Mutant lysC and Mutant dapA Derived from *E. coli*

Cell-free extracts were prepared from the *Methylophilus methylotrophus* AS1 strain containing the RSFD80 plasmid (also referred to as "AS1/RSFD80" hereinafter) and the *Methylophilus methylotrophus* AS1 strain containing the pRS plasmid (also referred to as "AS1/pRS" hereinafter), and AK activity was measured. The cell-free extracts (crude enzyme solutions) were prepared as follows. The AS1/RSFD80 strain and AS1/pRS strain were each inoculated to 121 production medium of the above composition containing 20 mg/L of streptomycin, cultured at 37° C. for 34 hours with shaking, and then calcium carbonate was removed and cells were harvested.

The bacterial cells obtained as described above were washed with 0.2% KCl under a condition of 0° C., suspended in 20 mM potassium phosphate buffer (pH 7) containing 10 mM $MgSO_4$, 0.8 M $(NH_4)_2SO_4$ and 0.03 M β-mercaptoethanol, and disrupted by sonication (0° C., 200 W, 10 minutes). The sonicated cell suspension was centrifuged at 33,000 rpm for 30 minutes under a condition of 0° C., and the supernatant was separated. To the supernatant, ammonium sulfate was added to 80% saturation, and the mixture was left at 0° C. for 1 hour, and centrifuged. The pellet was dissolved in 20 mM potassium phosphate buffer (pH 7) containing 10 mM $MgSO_4$, 0.8 M $(NH_4)_2SO_4$ and 0.03 M β-mercaptoethanol.

The measurement of AK activity was performed in accordance with the method of Stadtman (Stadtman, E. R., Cohen, G. N., LeBras, G., and Robichon-Szulmajster, H., J. Biol. Chem., 236, 2033 (1961)). That is, a reaction solution of the following composition was incubated at 30° C. for 45 minutes, and color development was caused by adding a $FeCl_3$ solution (2.8 N HCl: 0.4 ml, 12% TCA: 0.4 ml, 5% $FeCl_3.6H_2O$/0.1 N HCl: 0.7 ml). The reaction solution was centrifuged, and absorbance of the supernatant was measured at 540 nm. The activity was represented in terms of the amount of hydroxamic acid produced in 1 minute (1 U=1 μmol/minute). The molar extinction coefficient was set to be 600. The reaction solution not containing potassium aspartate was used as a blank. When the enzymatic activity was measured, L-lysine was added to the enzymatic reaction solution at various concentrations to examine degree of inhibition by L-lysine. The results are shown in Table 1.

| (Composition of reaction solution) | |
|---|---|
| Reaction mixture *[1] | 0.3 ml |
| Hydroxylamine solution *[2] | 0.2 ml |
| 0.1 M Potassium aspartate (pH 7.0) | 0.2 ml |
| Enzyme solution | 0.1 ml |
| Water (balance) | Total 1 ml |

*[1] 1 M Tris-HCl (pH 8.1): 9 ml, 0.3 M $MgSO_4$: 0.5 ml and 0.2 M ATP (pH 7.0): 5 ml
*[2] 8 M Hydroxylamine solution neutralized with KOH immediately before use

TABLE 1

| Strain | AK activity (Specific activity*[1]) | Specific activity with 5 mM L-lysine | Desensitization degree of inhibition*[2] (%) |
|---|---|---|---|
| AS1/pRS | 7.93 | 9.07 | 114 |
| AS1/RSFD80 | 13.36 | 15.33 | 115 |

*[1]nmol/minute/mg protein
*[2]Activity retention ratio in the presence of 5 mM L-lysine As shown in Table 1, AK activity was increased by about 1.7 times by the introduction of the RSFD80 plasmid. Further, it was confirmed that the inhibition by L-lysine was completely desensitized in AK derived from *E. coli* that was encoded by the RSFD80 plasmid. Moreover, it was found that AK that was originally retained by the AS1 strain was not inhibited by L-lysine alone. The inventors of the present invention have discovered that the AK derived from the AS1 strain was inhibited by 100% when 2 mM for each of L-lysine and L-threonine were present in the reaction solution (concerted inhibition).

(3) Production of L-Lysine by *Methylophilus* Bacterium Containing Mutant lysC and Mutant dapA Derived from *E. coli*

Then, the AS1/RSFD80 strain and the AS1/pRS strain were inoculated to 121 production medium containing 20 mg/L of streptomycin, and cultured at 37° C. for 34 hours with shaking. After the culture was completed, the bacterial cells and calcium carbonate were removed by centrifugation, and L-lysine concentration in the culture supernatant was measured by an amino acid analyzer (JASCO Corporation [Nihon Bunko], high performance liquid chromatography). The results are shown in Table 2.

TABLE 2

| Strain | Production amount of L-lysine hydrochloride (g/L) |
|---|---|
| AS1/pRS | 0 |
| AS1/RSFD80 | 0.3 |

Example 2

Creation of L-Lysine-Producing Bacterium (2)

(1) Introduction of tac Promoter Region into Broad Host Spectrum Vector

In order to produce a large amount of enzyme involved in the biosynthesis of L-lysine (Lys) in *Methylophilus methylotrophus*, tac promoter was used for gene expression of the target enzyme. The promoter is frequently used in *E. coli.*

The tac promoter region was obtained by amplification through PCR using DNA of pKK233-3 (Pharmacia) as a template, DNA fragments having the nucleotide sequences of SEQ ID NOS: 15 and 16 as primers, and a heat-resistant DNA polymerase. The PCR was performed with a cycle of 94° C. for 20 seconds, 60° C. for 30 seconds, and 72° C. for 60 seconds, which was repeated 30 times. Then, the amplified DNA fragment was collected and treated with restriction enzymes EcoRI and PstI. On the other hand, a broad host spectrum vector pRS (see Japanese Patent Application Laid-open (Kohyo) No. 3-501682/1991) was also digested with the same restriction enzymes, and the aforementioned DNA fragment which contained the tac promoter region was introduced into the restriction enzyme digestion termini to construct pRS-tac.

(2) Preparation of dapA Gene (Dihydrodipicolinate Synthase Gene) Expression Plasmid pRS-dapA24 and lysC Gene (Aspartokinase Gene) Expression Plasmid pRS-lysC80

A mutant gene (dapA*24) coding for dihydrodipicolinate synthase whose feedback inhibition for the enzyme activity by Lys was partially desensitized was introduced into the plasmid pRS-tac which was prepared by the method described in the above (1).

First, the dapA*24 gene region was obtained by amplification through PCR using DNA of RSFD80 (see Example 1) as a template, and DNA fragments having the nucleotide sequences of SEQ ID NOS: 17 and 18 as primers. The PCR was performed with a cycle of 94° C. for 20 seconds, 60° C. for 30 seconds, and 72° C. for 90 seconds, which was repeated 30 times. Then, the fragment was treated with restriction enzymes Sse8387I and XbaI to prepare a dapA*24 gene fragment having corresponding cleaved termini. On the other hand, pRS-tac was also treated with Sse8387I and partially digested with XbaI in the same manner as described above. To this digested plasmid, the aforementioned dapA*24 gene fragment was ligated by using T4 ligase to obtain pRS-dapA24.

Similarly, a gene (lysC*80) coding for aspartokinase whose feedback inhibition for the enzyme activity by Lys was partially desensitized was obtained by PCR using DNA of RSFD80 as a template, and DNA fragments having the nucleotide sequences of SEQ ID NOS: 19 and 20 as primers. The PCR was performed with a cycle of 94° C. for 20 seconds, 60° C. for 30 seconds, and 72° C. for 90 seconds, which was repeated 30 times. Then, the obtained DNA fragment was treated with restriction enzymes Sse8387I and SapI. On the other hand, the vector pRS-tac was also treated with Sse8387I and SapI. To this digested plasmid, the aforementioned lysC*80 gene fragment was ligated by using T4 ligase to obtain pRS-lysC80.

(3) Introduction of pRS-dapA24 or pRS-lysC80 into *Methylophilus methylotrophus* and Evaluation of Culture Each of pRS-dapA24 and pRS-lysC80 obtained as described above was introduced into the *Methylophilus methylotrophus* AS1 strain (NCIMB10515) by electroporation to obtain AS1/pRS-dapA24 and AS1/pRS-lysC80, respectively. Each strain was inoculated to 121 production medium containing 20 mg/L of streptomycin, and cultured at 37° C. for 48 hours with shaking. As a control strain, AS1 strain harboring pRS was also cultured in a similar manner. After the culture was completed, the cells and calcium corbonate were removed by centrifugation, and L-lysine concentration in the culture supernatant was measured by an amino acid analyzer (JASCO Corporation [Nihon Bunko], high performance liquid chromatography). The results are shown in Table 3.

TABLE 3

| Strain | Production amount of L-lysine hydrochloride (g/L) |
|---|---|
| AS1/pRS | <0.01 |
| AS1/pRS-lysC80 | 0.06 |
| AS1/pRS-dapA24 | 0.13 |

Example 3

Creation of L-Lysine-Producing Bacterium (3)

The *Methylophilus methylotrophus* AS1 strain (NCIMB10515) was inoculated to 121M1 medium and cultured at 37° C. for 15 hours. The obtained bacterial cells were treated with NTG in a conventional manner (NTG concentration: 100 mg/L, 37° C., 5 minutes), and spread onto 121M1 agar medium containing 7 g/L of S-(2-aminoethyl)-cysteine (AEC) and 3 g/L of L-threonine. The cells were cultured at 37° C. for 2 to 8 days, and the formed colonies were picked up to obtain AEC-resistant strains.

The aforementioned AEC-resistant strains were inoculated to 121 production medium, and cultured at 37° C. for 38 hours under an aerobic condition. After the culture was completed, the cells and calcium carbonate were removed from the medium by centrifugation, and L-lysine concentration in the culture supernatant was measured by an amino acid analyzer (JASCO Corporation [Nihon Bunko], high performance liquid chromatography). A strain showing improved L-lysine-producing ability compared with the parent strain was selected, and designated as *Methylophilus methylotrophus* AR-166 strain. The L-lysine production amounts of the parent strain (AS1 strain) and the AR-166 strain are shown in Table 4.

TABLE 4

| Strain | Production amount of L-lysine hydrochloride (mg/L) |
|---|---|
| AS1 | 5.8 |
| AR-166 | 80 |

The *Methylophilus methylotrophus* AR-166 strain was given a private number of AJ13608, and was deposited at National Institute of Bioscience and Human-Technology, Agency of Industrial science and Technology, Ministry of International Trade and Industry (postal code 305-8566, 1-3 Higashi 1-chome, Tsukuba-shi, Ibaraki-ken, Japan) on Jun. 10, 1999 and received an accession number of FERM P-17416, and it was transferred to an international deposition under the provisions of the Budapest Treaty on Mar. 31, 2000, and received an accession number of FERM BP-7112.

Example 4

Creation of L-Threonine-Producing Bacterium (1) Introduction of Threonine Operon Plasmid into *Methylophilus* Bacterium A plasmid pVIC40 (International Publication WO90/04636, Japanese Patent Application Laid-open (Kohyo) No. 3-501682/1991) containing a threonine operon derived from *E. coli* was introduced into the *Methylophilus methylotrophus* AS1 strain (NCIMB10515) by electroporation (Canadian Journal of Microbiology, 43, 197 (1997)) to obtain AS1/pVIC40 strain. As a control, pRS (Japanese Patent Application Laid-open (Kohyo) No. 3-501682/1991) having only the vector region was obtained by deleting the DNA region coding for the threonine operon from the pVIC40 plasmid, and it was introduced into the AS1 strain in the same manner as used for pVIC40 to obtain AS1/pRS strain.

(2) Production of L-Threonine by *Methylophilus* Bacterium Containing Threonine Operon Derived from *E. coli*

Each of the AS1/pVIC40 and AS1/pRS strains was inoculated to 121 production medium containing 20 mg/L of streptomycin, 1 g/l of L-valine and 1 g/l of L-leucine, and cultured at 37° C. for 50 hours with shaking. After the culture was completed, the cells and calcium carbonate were removed by centrifugation, and L-threonine concentration in the culture supernatant was measured by an amino acid analyzer (JASCO Corporation [Nihon Bunko], high performance liquid chromatography). The results are shown in Table 5.

TABLE 5

| Strain | Production amount of L-threonine (mg/L) |
|---|---|
| AS1/pRS | 15 |
| AS1/pVIC40 | 30 |

Example 5

Creation of Branched Chain Amino Acid-Producing Bacterium

The *Methylophilus methylotrophus* AS1 strain (NCIMB10515) was inoculated to 121M1 medium and cultured at 37° C. for 15 hours. The obtained bacterial cells were treated with NTG in a conventional manner (NTG concentration: 100 mg/L, 37° C., 5 minutes), and spread onto 121M1 agar medium containing 0.5% of casamino acid (DIFCO). The cells were cultured at 37° C. for 2 to 8 days, and allowed to form colonies. The formed colonies were picked up, and inoculated to 121M1 agar medium and 121M1 agar medium containing 0.5% of casamino acid. Strains exhibiting better growth on the latter medium compared with on the former medium were selected as casamino acid auxotrophic strains. In this way, 9 leaky casamino acid auxotrophic strains were obtained from NTG-treated 500 strains. From these casamino acid auxotrophic strains, one strain that accumulated more L-valine, L-leucine and L-isoleucine in the medium compared with its parent strain was obtained. This strain was designated as *Methylophilus methylotrophus* C138 strain.

The *Methylophilus methylotrophus* C138 strain was given a private number of AJ13609, and was deposited at National Institute of Bioscience and Human-Technology, Agency of Industrial Science and Technology, Ministry of International Trade and Industry (postal code 305-8566, 1-3 Higashi 1-chome, Tsukuba-shi, Ibaraki-ken, Japan) on Jun. 10, 1999 and received an accession number of FERM P-17417, and it was transferred to an international deposition under the provisions of the Budapest Treaty on Mar. 31, 2000, and received an accession number of FERM BP-7113.

The parent strain (AS1 strain) and the C138 strain were inoculated to 121 production medium, and cultured at 37° C. for 34 hours under an aerobic condition. After the culture was completed, the cells and calcium carbonate were removed from the medium by centrifugation, and concentrations of L-valine, L-leucine and L-isoleucine in the culture supernatant were measured by an amino acid analyzer (JASCO Corporation [Nihon Bunko], high performance liquid chromatography). The results are shown in Table 6.

TABLE 6

| Strain | L-valine (mg/L) | L-leucine (mg/L) | L-isoleucine (mg/L) |
|---|---|---|---|
| AS1 | 7.5 | 5.0 | 2.7 |
| C138 | 330 | 166 | 249 |

Example 6

Preparation of Chromosome DNA Library of *Methylophilus methylotrophus* AS1 Strain (1) Preparation of Chromosome DNA of *Methylophilus methylotrophus* AS1 Strain One platinum loop of the *Methylophilus methylotrophus* AS1 strain (NCIMB10515) was inoculated to ml of 121M1 medium in a test tube, and cultured at 37° C. overnight with shaking. The obtained culture broth was inoculated to 50 ml of 121M1 medium in a 500 ml-volume Sakaguchi flask in an amount of 1%, and cultured at 37° C. overnight with shaking. Then, the cells were harvested by centrifugation, and suspended in 50 ml of TEN solution (solution containing 50 mM Tris-HCl (pH 8.0), 10 mM EDTA and 20 mM NaCl (pH 8.0)). The cells were collected by centrifugation, and suspended again in 5 ml of the TEN solution containing 5 mg/ml of lysozyme and 10 μg/ml of RNase A. The suspension was maintained at 37° C. for 30 minutes, and then proteinase K and sodium laurylsulfate were added thereto to final concentrations of 10 μg/ml and 0.5% (wt/vol), respectively.

The suspension was maintained at 70° C. for 2 hours, and then an equal amount of a saturated solution of phenol (phenol solution saturated with 10 mM Tris-HCl (pH 8.0)) was added and mixed. The suspension was centrifuged, and the supernatant was collected. An equal amount of phenol/chloroform solution (phenol:chloroform:isoamyl alcohol=25:24:1) was added and mixed, and the mixture was centrifuged. The supernatant was collected, and an equal amount of chloroform solution (chloroform:isoamyl alcohol=24:1) was added thereto to repeat the same extraction procedure. To the supernatant, a 1/10 volume of 3 M sodium acetate (pH 4.8) and 2.5-fold volume of ethanol were added to precipitate chromosome DNA. The precipitates were collected by centrifugation, washed with 70% ethanol, dried under reduced pressure, and dissolved in a suitable amount of TE solution (10 mM Tris-HCl, 1 mM EDTA (pH 8.0)).

(2) Preparation of Gene Library

A 50 μl portion of the chromosome DNA (1 μg/μl) obtained in the above (1), 20 μl of H buffer (500 mM Tris-HCl, 100 mM $MgCl_2$, 10 mM dithiothreitol, 1000 mM NaCl (pH 7.5)) and 8 units of a restriction enzyme Sau3AI (Takara Shuzo) were allowed to react at 37° C. for 10 minutes in a total volume of 200 μl, and then 200 μl of the phenol/chloroform solution was added and mixed to stop the reaction. The reaction mixture was centrifuged, and the upper layer was collected and separated on a 0.8% agarose gel. DNA corresponding to 2 to 5 kilobase pair (henceforth abbreviated as "kbp") was collected by using Concert™ Rapid Gel Extraction System (DNA collecting kit, GIBCO BRL Co.). In this way, 50 μl of a solution of DNA with fractionated size was obtained.

On the other hand, 2.5 μg of plasmid pUC118 (Takara Shuzo), 2 μl of K buffer (200 mM Tris-HCl, 100 mM $MgCl_2$, 10 mM dithiothreitol, 1000 mM KCl (pH 8.5)) and 10 units of restriction enzyme BamHI (Takara Shuzo) were allowed to react at 37° C. for 2 hours in a total volume of 20 μl, then 20 units of calf small intestine alkaline phosphatase (Takara Shuzo) was added and mixed, and the mixture was allowed to react for further 30 minutes. The reaction mixture was mixed with an equal amount of the phenol/chloroform solution, and the mixture was centrifuged. The supernatant was collected, and an equal amount of the chloroform solution was added thereto to repeat a similar extraction procedure. To the supernatant, a 1/10 volume of 3 M sodium acetate (pH 4.8) and 2.5-fold volume of ethanol were added to precipitate DNA. The DNA was collected by centrifugation, washed with 70% ethanol, dried under reduced pressure, and dissolved in a suitable amount of TE solution.

A Sau3AI digestion product of the chromosome DNA prepared as described above and a BamHI digestion product of pUC118 were ligated by using a Ligation Kit ver. 2 (Takara Shuzo). To the reaction mixture, a 1/10 volume of 3 M sodium acetate (pH 4.8) and 2.5-fold volume of ethanol were added to precipitate DNA. The DNA was collected by centrifugation, washed with 70% ethanol, dried under reduced pressure, and dissolved in TE solution (Ligase solution A).

In the same manner as in the above procedure, fragments obtained by partial digestion of the chromosome DNA with a restriction enzyme AluI (Takara Shuzo) and a SmaI digestion product of plasmid pSTV29 (Takara Shuzo) were ligated (Ligase solution B).

One platinum loop of *E. coli* JM109 was inoculated to 5 ml of L medium in a test tube, and cultured at 37° C. overnight with shaking. The obtained culture broth was inoculated to 50 ml of L medium in a 500 ml-volume Sakaguchi flask in an amount of 1%, cultured at 37° C. until $OD_{660}$ of the culture became 0.5 to 0.6, and cooled on ice for 15 minutes. Then, the cells were harvested by centrifugation at 4° C. The cells were suspended in 50 ml of ice-cooled water and centrifuged to wash the cells. This operation was repeated once again, and the cells were suspended in 50 ml of ice-cooled 10% glycerol solution, and centrifuged to wash the cells. The cells were suspended in 10% glycerol solution of the same volume as the cells, and divided into 50 μl aliquots. To the cells in the 50 μl volume, 1 μl of Ligase solution A or Ligase solution B prepared above was added. Then, the mixture was put into a special cuvette (0.1 cm width, preliminarily ice-cooled) for an electroporation apparatus of BioRad.

The setting of the apparatus was 1.8 kV and 25 μF, and the setting of pulse controller was 200 ohms. The cuvette was mounted on the apparatus and pulses were applied thereto. Immediately after the application of pulse, 1 ml of ice-cooled SOC medium was added thereto, and the mixture was transferred into a sterilized test tube, and cultured at 37° C. for 1 hour with shaking. Each cell culture broth was spread onto L agar medium containing an antibiotic (100 μg/ml of ampicillin when Ligase solution A was used, or 20 μg/ml of chloramphenicol when Ligase solution B was used), and incubated at 37° C. overnight. The colonies emerged on each agar medium were scraped, inoculated to 50 ml of L medium containing respective antibiotic in a 500 ml-volume Sakaguchi flask, and cultured at 37° C. for 2 hours with shaking. Plasmid DNA was extracted from each culture broth by the alkali SDS method to form Gene library solution A and Gene library solution B, respectively.

Example 7

Cloning of Lysine Biosynthesis Gene of *Methylophilus methylotrophus* AS1 Strain (1) Cloning of Gene Coding for Aspartokinase (AK)

*E. coli* GT3 deficient in the three genes coding for AK (thrA, metLM and lysC) was transformed with Gene library solution B by the same electroporation procedure as mentioned above. SOC medium containing 20 μg/ml of diaminopimelic acid was added to the transformation solution, and cultured at 37° C. with shaking. Then, the culture broth was spread onto L medium containing 20 μg/ml of diaminopimelic acid and 20 μg/ml of chloramphenicol to obtain emerged colonies. This was replicated as a master plate to M9 agar medium containing 20 μg/ml of chloramphenicol, and the replicate was incubated at 37° C. for 2 to 3 days. The host could not grow in M9 minimal medium that did not contain diaminopimelic acid since it did not have AK activity. In contrast, it was expected that the transformant strain that contained the gene coding for AK derived from *Methylophilus methylotrophus* could grow in M9 minimal medium because of the function of the gene.

Figure 3:
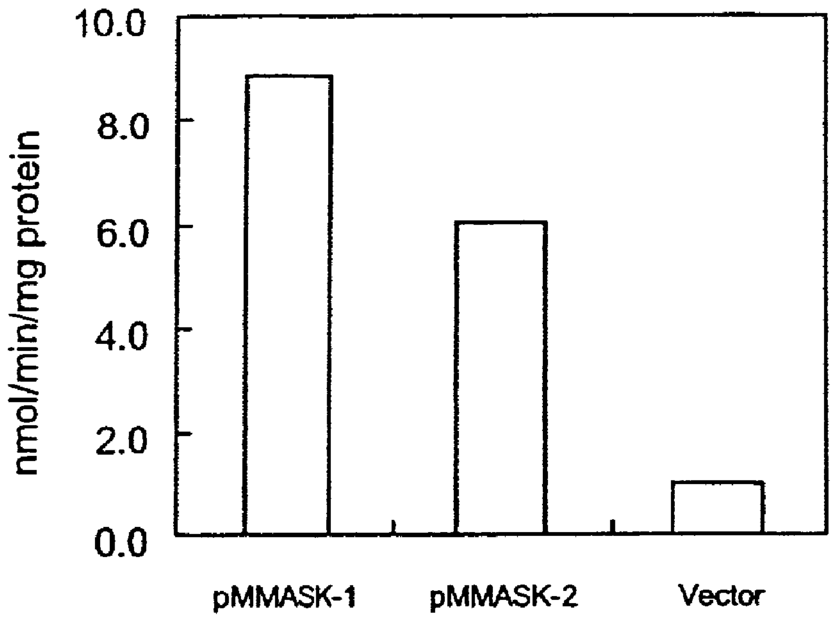
FIG. 3 shows aspartokinase activity of transformant *E. coli* strains containing an ask gene.

Two transformants out of about 3000 transformants formed colonies on M9 medium. Plasmids were extracted from the colonies emerged on M9 medium and analyzed. As a result, the presence of an inserted fragment on the plasmids was confirmed. The plasmids were designated as pMMASK-1 and pMMASK-2, respectively. By using these plasmids, *E. coli* GT3 was transformed again. The obtained transformants could grow on M9 minimal medium. Further, the transformant which contained each of these plasmids was cultured overnight in L medium containing 20 μg/ml of chloramphenicol, and the cells were collected by centrifugation of the culture broth. Cell-free extracts were prepared by sonicating the cells, and AK activity was measured according to the method of Miyajima et al. (Journal of Biochemistry (Tokyo), vol. 63, 139–148 (1968)) (FIG. 3: pMMASK-1, pMMASK-2). In addition, a GT3 strain harboring the vector pSTV29 was similarly cultured in L medium containing 20 μg/ml of diaminopimelic acid and 20 μg/ml of chloramphenicol, and AK activity was measured (FIG. 3: Vector). As a result, increase in AK activity was observed in two of the clones containing the inserted fragments compared with the transformant harboring only the vector. Therefore, it was confirmed that the gene that could be cloned on pSTV29 was a gene coding for AK derived from *Methylophilus methylotrophus*. This gene was designated as ask.

The DNA nucleotide sequence of the ask gene was determined by the dideoxy method. It was found that pMMASK-1 and pMMASK-2 contained a common fragment. The nucleotide sequence of the DNA fragment containing the ask gene derived from *Methylophilus methylotrophus* is shown in SEQ ID NO: 5. An amino acid sequence that can be encoded by the nucleotide sequence is shown in SEQ ID NOS: 5 and 6.

(2) Cloning of Gene Coding for Aspartic Acid Semialdehyde Dehydrogenase (ASD)

*E. coli* Hfr3000 U482 (CGSC 5081 strain) deficient in the asd gene was transformed by electroporation using Gene library solution B in the same manner as described above. To the transformation solution, SOC medium containing 20 μg/ml of diaminopimelic acid was added and the mixture was cultured at 37° C. with shaking. The cells were harvested by centrifugation. The cells were washed by suspending them in L medium and centrifuging the suspension. The same washing operation was repeated once again, and the cells were suspended in L medium. Then, the suspension was spread onto L agar medium containing 20 μg/ml of chloramphenicol, and incubated overnight at 37° C. The host showed extremely slow growth in L medium not containing diaminopimelic acid since it was deficient in the asd gene. In contrast, it was expected that normal growth would be observed for a transformant strain which contained the gene coding for ASD derived from *Methylophilus methylotrophus* even in L medium because of the function of the gene. Further, the host *E. coli* could not grow in M9 minimal medium, but a transformant strain that contained the gene coding for ASD derived from *Methylophilus methylotrophus* was expected to be able to grow in M9 minimal medium because of the function of the gene. Therefore, colonies of transformants that normally grew on L medium were picked up, streaked and cultured on M9 agar medium. As a result, growth was observed. Thus, it was confirmed that the gene coding for ASD functioned in these transformant strains as expected.

Figure 4:
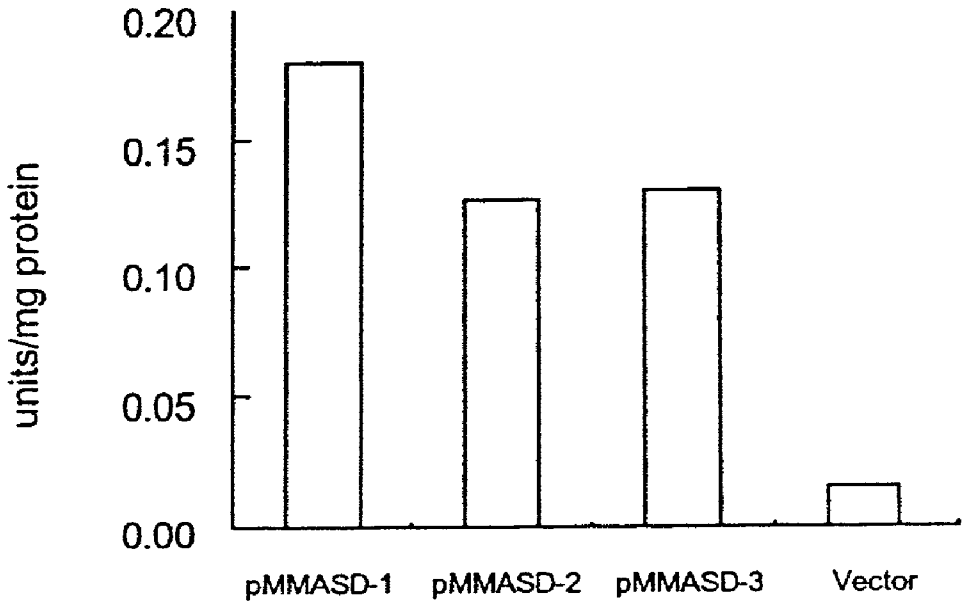
FIG. 4 shows aspartic acid semialdehyde dehydrogenase activity of transformant *E. coli* strains containing an asd gene.

Plasmids were extracted from the three transformant strains emerged on M9 medium, and the presence of an inserted fragment in the plasmids was confirmed. The plasmids were designated as pMMASD-1, pMMASD-2 and pMMASD-3, respectively. When the *E. coli* Hfr3000 U482 was transformed again by using these plasmids, each transformant grew in M9 minimal medium. Further, each transformant was cultured overnight in L medium containing 20

μg/ml of chloramphenicol, and the cells were collected by centrifugation of the culture broth. The cells were sonicated to prepare a crude enzyme solution, and ASD activity was measured according to the method of Boy et al. (Journal of Bacteriology, vol. 112 (1), 84–92 (1972)) (FIG. 4: pMMASD-1, pMMASD-2, pMMASD-3). In addition, the host harboring the vector was similarly cultured in L medium containing 20 μg/ml of diaminopimelic acid and 20 μg/ml of chloramphenicol, and ASD activity was measured as a control experiment (FIG. 4: Vector). As a result, the enzymatic activity could not be detected for the transformant harboring only the vector, whereas the ASD activity could be detected in three of the clones having an insert fragment. Therefore, it was confirmed that the obtained gene was a gene coding for ASD derived from *Methylophilus methylotrophus* (designated as asd).

The DNA nucleotide sequence of the asd gene was determined by the dideoxy method. It was found that all of the three obtained clones contained a common fragment. The nucleotide sequence of the DNA fragment containing the asd gene derived from *Methylophilus methylotrophus* is shown in SEQ ID NO: 7. An amino acid sequence that can be encoded by the nucleotide sequence is shown in SEQ ID NOS: 7 and 8.

(3) Cloning of Gene Coding for Dihydrodipicolinate Synthase (DDPS)

*E. coli* AT997 (CGSC 4547 strain) deficient in the dapA gene was transformed by the same electroporation procedure using Gene library solution A. To the transformation solution, SOC medium containing 20 μg/ml of diaminopimelic acid was added, and the mixture was cultured at 37° C. with shaking. Then, the culture broth was spread onto L medium containing 20 μg/ml of diaminopimelic acid and 100 μg/ml of ampicillin to obtain emerged colonies. This was replicated as a master plate to M9 minimal agar medium containing 100 μg/ml of ampicillin, and the replicate was incubated at 37° C. for 2 to 3 days. The host could not grow in M9 minimal medium that did not contain diaminopimelic acid since it was deficient in dapA gene. In contrast, it was expected that a transformant strain that contained the gene coding for DDPS derived from *Methylophilus methylotrophus* could grow in M9 minimal medium because of the function of that gene.

Figure 5:
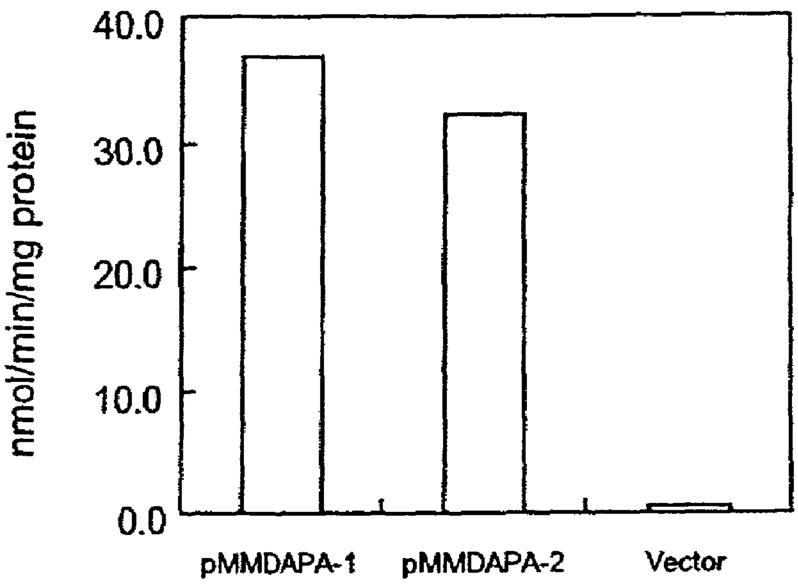
FIG. 5 shows dihydrodipicolinate synthase activity of transformant *E. coli* strains containing a dapA gene.

Plasmids were extracted from the colonies of two strains emerged on M9 medium, and analyzed. As a result, the presence of an inserted fragment in the plasmids was confirmed. The plasmids were designated as pMMDAPA-1 and pMMDAPA-2, respectively. When *E. coli* AT997 was transformed again by using these plasmids, each transformant was grown in M9 minimal medium. Further, each transformant containing each plasmid was cultured overnight in L medium containing 100 μg/ml of ampicillin, and the cells were collected by centrifugation of the culture both. The cells were sonicated to prepare a cell extract, and DDPS activity was measured according to the method of Yugari et al. (Journal of Biological Chemistry, vol. 240, and p. 4710 (1965)) (FIG. 5: pMMDAPA-1, pMMDAPA-2). In addition the host harboring the vector was similarly cultured in L medium containing 20 μg/ml of diaminopimelic acid and 100 μg/ml of ampicillin, and DDPS activity was measured as a control experiment (FIG. 5: Vector). As a result, the enzymatic activity could not be detected for the transformant harboring only the vector, whereas the DDPS activity could be detected in each of the transformants harboring the plasmids having the insert fragment. Therefore, it was confirmed that the obtained gene was a gene coding for DDPS derived from *Methylophilus methylotrophus* (designated as dapA).

The DNA nucleotide sequence of the dapA gene was determined by the dideoxy method. It was found that two of the inserted fragments contained a common fragment. The nucleotide sequence of the DNA fragment containing the dapA gene derived from *Methylophilus methylotrophus* is shown in SEQ ID NO: 9. An amino acid sequence that can be encoded by the nucleotide sequence is shown in SEQ ID NOS: 9 and 10.

(4) Cloning of Gene Coding for Dihydrodipicolinate Reductase (DDPR)

*E. coli* AT999 (CGSC 4549 strain) deficient in the dapB gene was transformed by the same electroporation procedure as described above using Gene library solution A. To the transformation solution, SOC medium containing 20 μg/ml of diaminopimelic acid was added, and the mixture was cultured at 37° C. with shaking. Then, the cells were harvested by centrifugation. The cells were washed by suspending them in L medium and centrifuging the suspension. The same washing operation was repeated once again, and the cells were suspended in L medium. Then, the suspension was spread onto L agar medium containing 100 μg/ml of ampicillin, and incubated overnight at 37° C. The host showed extremely slow growth in L medium not containing diaminopimelic acid since it was deficient in the dapB gene. In contrast, it was expected that normal growth could be observed for a transformant strain that contained the gene coding for DDPR derived from *Methylophilus methylotrophus* even in L medium because of the function of the gene. Further, the host *E. coli* could not grow in M9 minimal medium, but it was expected that a transformant strain which contained the gene coding for DDPR derived from *Methylophilus methylotrophus* could grow in M9 minimal medium because of the function of the gene.

Figure 6:
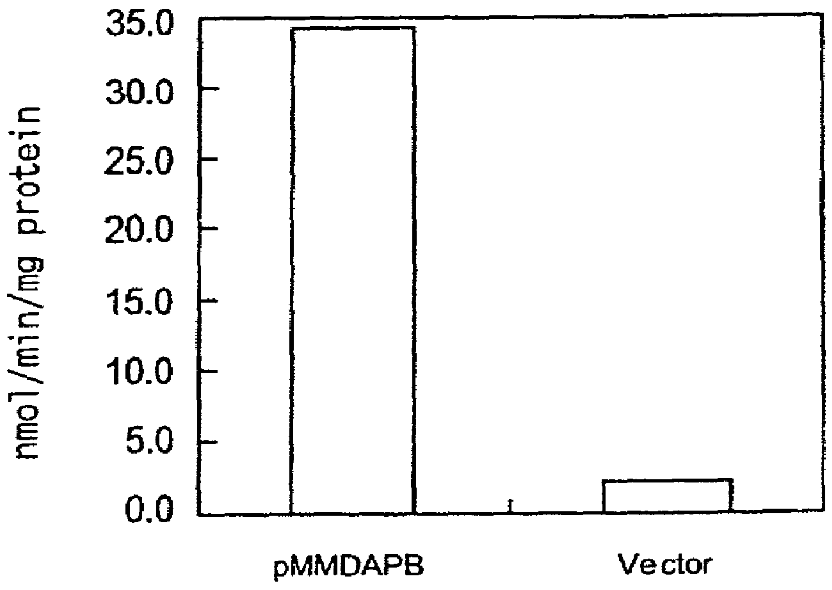
FIG. 6 shows dihydrodipicolinate reductase activity of a transformant *E. coli* strain containing a dapB gene.

Therefore, a colony of transformant that normally grew on L medium was streaked and cultured on M9 agar medium. Then, growth was also observed on M9 medium. Thus, it was confirmed that the gene coding for DDPR functioned in the transformant strain. A plasmid was extracted from the colony emerged on M9 medium, and the presence of an inserted fragment in the plasmid was confirmed. When *E. coli* AT999 was transformed again by using the plasmid (pMMDAPB), the transformant grew in M9 minimal medium. Further, the transformant containing the plasmid was cultured overnight in L medium, and the cells were collected by centrifugation of the culture broth. The cells were sonicated to prepare a cell extract, and DDPR activity was measured according to the method of Tamir et al. (Journal of Biological Chemistry, vol. 249, p. 3034 (1974)) (FIG. 6: pMMDAPB). In addition, the host harboring the vector was similarly cultured in L medium containing 20 μg/ml diaminopimelic acid and 100 μg/ml of ampicillin, and DDPR activity was measured as a control experiment (FIG. 6: Vector). As a result, the enzymatic activity could not be detected for the transformant harboring only the vector, whereas the DDPR activity could be detected for the transformant harboring pMMDAPB. Therefore, it was confirmed that the obtained gene was a gene coding for DDPR derived from *Methylophilus methylotrophus* (designated as dapB).

The DNA nucleotide sequence of the dapB gene was determined by the dideoxy method. The nucleotide sequence of the DNA fragment containing the dapB gene derived from *Methylophilus methylotrophus* is shown in SEQ ID NO: 11. An amino acid sequence that can be encoded by the nucleotide sequence is shown in SEQ ID NOS: 11 and 12.

(5) Cloning of Gene Coding for Diaminopimelate Decarboxylase (DPDC)

*E. coli* AT2453 (CGSC 4505 strain) deficient in the lysA gene was transformed by the same electroporation procedure as described above using Gene library solution A. The transformation solution, SOC medium was added, and the mixture was cultured at 37° C. with shaking. The cells were harvested by centrifugation. The cells were washed by suspending them in 5 ml of sterilized water and centrifuging the suspension. The same washing operation was repeated once again, and the cells were suspended in 500 μl of sterilized water. Then, the suspension was spread onto M9 minimal agar medium containing 20 μg/ml of chloramphenicol, and incubated at 37° C. for 2 to 3 days. The host could not grow in M9 minimal medium not containing lysine since it was deficient in the lysA gene. In contrast, it was expected that a transformant strain that contained the gene coding for DPDC derived from *Methylophilus methylotrophus* could grow in M9 minimal medium because of the function of the gene.

Figure 7:
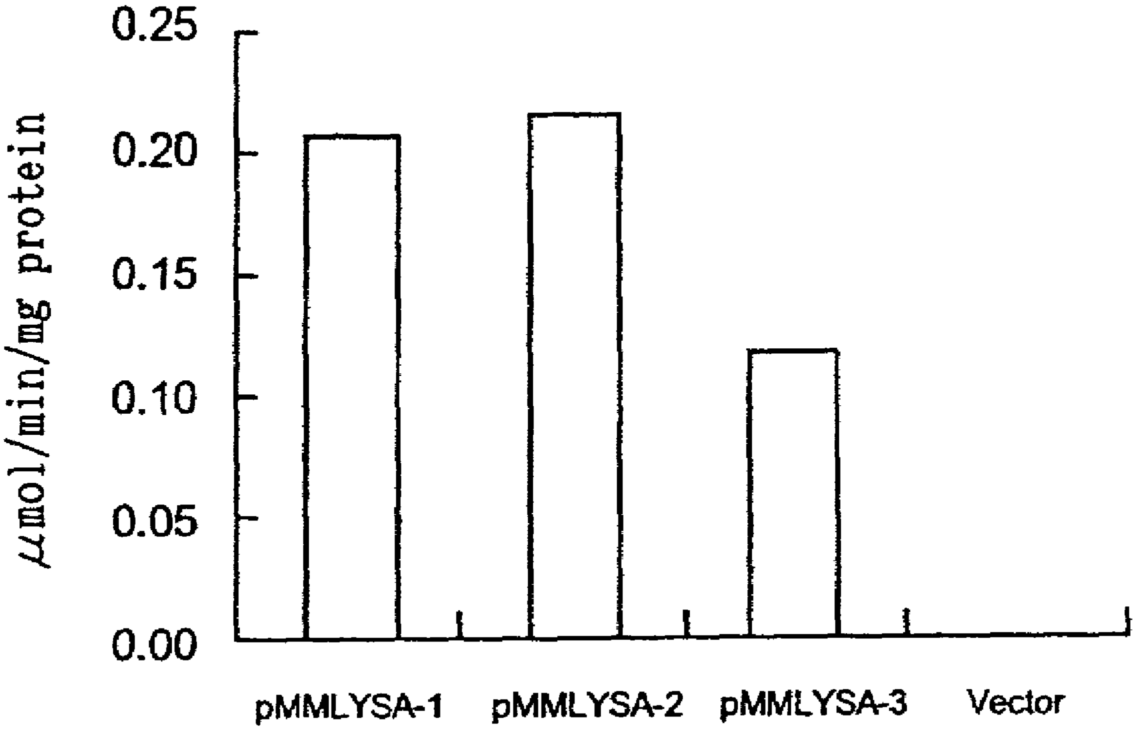
FIG. 7 shows diaminopimelate decarboxylase activity of transformant *E. coli* strains containing a lysA gene.

Therefore, plasmids were extracted from the three transformant strains emerged on M9 medium, and analyzed. As a result, the presence of an inserted fragment in the plasmids was confirmed. The plasmids were designated as pMMLYSA-1, pMMLYSA-2 and pMMLYSA-3, respectively. When *E. coli* AT2453 was transformed again by using each of these plasmids, each transformant grew in M9 minimal medium. Further, each transformant containing each plasmid was cultured overnight in L medium containing 20 μg/ml of chloramphenicol, and the cells were collected by centrifugation of the culture broth. The cells were sonicated to prepare a cell extract, and DPDC activity was measured according to the method of Cremer et al. (Journal of General Microbiology, vol. 134, 3221–3229 (1988)) (FIG. 7: pMMLYSA-1, pMMLYSA-2, pMMLYSA-3). In addition, the host harboring the vector was similarly cultured in L medium containing 20 μg/ml of chloramphenicol, and DPDC activity was measured as a control experiment (FIG. 7: Vector). As a result, the enzymatic activity could not be detected for the transformant harboring only the vector, whereas the DPDC activity could be detected in three of the clones having an insert fragment. Therefore, it was confirmed that the obtained gene was a gene coding for DPDC derived from *Methylophilus methylotrophus* (designated as lysA).

The DNA nucleotide sequence of the lysA gene was determined by the dideoxy method. It was found that all of the three inserted fragments contained a common DNA fragment. The nucleotide sequence of the DNA fragment containing the lysA gene derived from *Methylophilus methylotrophus* is shown in SEQ ID NO: 13. An amino acid sequence that can be encoded by the nucleotide sequence is shown in SEQ ID NOS: 13 and 14.

INDUSTRIAL APPLICABILITY

According to the present invention, there are provided a *Methylophilus* bacterium having L-amino acid-producing ability, a method for producing an L-amino acid using the *Methylophilus* bacterium, and *Methylophilus* bacterial cells with increased content of an L-amino acid. By the method of the present invention, it is enabled to produce an L-amino acid using methanol as a raw material. Moreover, novel L-lysine biosynthesis enzyme genes derived from *Methylophilus* bacteria are provided by the present invention.

What is claimed is:

1. An isolated strain of *Methylophilus methylotrophus* having L-lysine-producing ability, wherein dihydrodipicolinate synthase activity is enhanced as compared to a wild-type *Methylophilus methylotrophus* strain, and wherein said dihydrodipicolinate synthase is selected from the group consisting of:

a) a protein encoded by a DNA comprising nucleotides 1268 to 2155 of SEQ ID NO:9; and b) a protein having dihydrodipicolinate synthase activity and encoded by a DNA comprising nucleotide numbers 1268 to 2155 of SEQ ID NO:9, except that substitution, deletion, or addition of one to 10 amino acids is present in the amino acid sequence of said protein, and wherein said activity is enhanced by a method selected from the group consisting of:

i) increasing the copy number of said DNA in said strain, ii) placing multiple copies of said DNA on the chromosome of said strain, and iii) replacing a native promoter with a stronger promoter upstream of said DNA.

2. An isolated strain of *Methylophilus methylotrophus* having L-lysine-producing ability, wherein dihydrodipicolinate synthase activity and aspartokinase activity are enhanced as compared to a wild-type *Methylophilus methylotrophus* strain, and wherein said dihydrodipicolinate synthase is selected from the group consisting of:

a) a protein encoded by a DNA comprising nucleotides 1268 to 2155 of SEQ ID NO:9; and b) a protein having dihydrodipicolinate synthase activity and encoded by a DNA comprising nucleotides 1268 to 2155 of SEQ ID NO:9, except that substitution, deletion, or addition of one to 10 amino acids is present in the amino acid sequence of said protein, and wherein said aspartokinase is selected from the group consisting of:

a) a protein encoded by a DNA comprising nucleotides 510 to 1736 of SEQ ID NO:5; and b) a protein having aspartokinase activity and encoded by a DNA comprising nucleotides 510 to 1736 of SEQ ID NO:5, except that substitution, deletion, addition, or inversion of one to 10 amino acids is present in the amino acid sequence of said protein, and wherein said activity is enhanced by a method selected from the group consisting of:

i) increasing the copy number of said DNA in said strain, ii) placing multiple copies of said DNA on the chromosome of said strain, and iii) replacing a native promoter with a stronger promoter upstream of said DNA.

3. An isolated strain of *Methylophilus methylotrophus* having L-amino acid-producing ability, wherein aspartokinase activity is enhanced as compared to wild-type *Methylophilus methylotrophus* strain, and wherein said aspartokinase is selected from the group consisting of:

a) a protein encoded by a DNA comprising nucleotides 510 to 1736 of SEQ ID NO:5; and b) a protein having aspartokinase activity and encoded by a DNA comprising nucleotides 510 to 1736 of SEQ ID NO:5, except that substitution, deletion, or addition of one to 10 amino acids is present in the amino acid sequence of said protein and wherein said activity is enhanced by a method selected from the group consisting of:

i) increasing the copy number of said DNA in said strain, ii) placing multiple copies of said DNA on the chromosome of said strain, and iii) replacing a native promoter with a stronger promoter upstream of said DNA.

4. The isolated strain according to claim 3, wherein the L-amino acid is L-lysine.

5. The isolated strain according to claim 2, wherein an activity or activities of one, two, or three enzymes selected from the group consisting of aspartic acid semialdehyde dehydrogenase, dihydrodipicolinate reductase, and diaminopimelate decarboxylase is/are enhanced as compared to a wild-type *Methylophilus methylotrophus* strain by a method selected from the group consisting of:

i) increasing the copy number(s) of a DNA(s) encoding said one, two, or three enzyme(s) in said strain, ii) placing multiple copies of said DNA(s) on the chromosome of said strain, and iii) replacing a native promoter with a stronger promoter upstream of said DNA(s).

6. The isolated strain according to claim 2, wherein the dihydrodipicolinate synthase activity and the aspartokinase activity are enhanced as compared to a wild-type *Methylophilus methylotrophus* strain by transformation with a DNA coding for said dihydrodipicolinate synthase and a DNA coding for said aspartokinase.

7. The isolated strain according to claim 3, wherein activities of homoserine dehydrogenase, homoserine kinase and threonine synthase are enhanced as compared to wild-type *Methylophilus methylotrophus* strain by a method selected from the group consisting of:

i) increasing the copy numbers of DNAs encoding homoserine dehydrogenase, homoserine kinase, and threonine synthase in said strain, ii) placing multiple copies of said DNAs on the chromosome of said strain, and iii) replacing a native promoter with a stronger promoter upstream of said DNAs, and wherein said isolated strain has L-threonine-producing ability.

8. A method for producing L-lysine, which comprises culturing said strain as defined in claim 1 in a medium, accumulating said L-lysine in said medium, and collecting the L-lysine from said medium.

9. The method according to claim 8, wherein the medium contains methanol as a main carbon source.

10. The isolated strain according to claim 1, wherein an activity or activities of one, two, or three of enzymes selected from the group consisting of aspartic acid semialdehyde dehydrogenase, dihydrodipicolinate reductase and diaminopimelate decarboxylase is/are enhanced as compared to a wild-type *Methylophilus methylotrophus* strain by a method selected from the group consisting of:

i) increasing the copy number(s) of a DNA(s) encoding said one, two, or three enzyme(s) in said strain, ii) placing multiple copies of said DNA(s) on the chromosome of said strain, and iii) replacing a native promoter with a stronger promoter upstream of said DNA(s).

11. The isolated strain according to claim 4, wherein an activity or activities of one, two, or three of enzymes selected from the group consisting of aspartic acid semialdehyde dehydrogenase, dihydrodipicolinate reductase and diaminopimelate decarboxylase is/are enhanced as compared to a wild-type *Methylophilus methylotrophus* strain by a method selected from the group consisting of:

i) increasing the copy number(s) of a DNA(s) encoding said one, two, or three enzyme(s) in said strain, ii) placing multiple copies of said DNA(s) on the chromosome of said strain, and iii) replacing a native promoter with a stronger promoter upstream of said DNA(s).

12. A method for producing L-lysine, which comprises culturing said strain as defined in claim 2 in a medium, accumulating said L-lysine in said medium, and collecting the L-lysine from said medium.

13. The method according to claim 12, wherein the medium contains methanol as a main carbon source.

14. A method for producing an L-amino acid, which comprises culturing said strain as defined in claim 3 in a medium, accumulating said L-amino acid in said medium, and collecting the L-amino acid from said medium.

15. The method according to claim 14, wherein the medium contains methanol as a main carbon source.

16. A method for producing L-lysine, which comprises culturing said strain as defined in claim 5 in a medium, accumulating L-lysine in said medium, and collecting L-lysine from said medium.

17. A method for producing L-lysine, which comprises culturing said strain as defined in claim 6 in a medium, accumulating L-lysine in said medium, and collecting L-lysine from said medium.

18. A method for producing L-lysine, which comprises culturing said strain as defined in claim 10 in a medium, accumulating L-lysine in said medium, and collecting L-lysine from said medium.

19. A method for producing L-lysine, which comprises culturing said strain as defined in claim 11 in a medium, accumulating L-lysine in said medium, and collecting L-lysine from said medium.

20. A method for producing L-threonine, which comprises culturing said strain as defined in claim 7 in a medium, accumulating L-threonine in said medium, and collecting L-threonine from said medium.

21. An isolated DNA which codes for a protein selected from the group consisting of:

(A) a protein comprising the amino acid sequence of SEQ ID NO: 6, and (B) a protein comprising the amino acid sequence of SEQ ID NO:6 except that substitution, deletion, insertion, or addition of one to 10 amino acids in said amino acid sequence is present, and wherein said protein has aspartokinase activity.

22. The DNA according to claim 21, wherein said DNA is selected from the group consisting of:

(a) a DNA comprising the nucleotides 510 to 1736 of SEQ ID NO:5; and (b) a DNA having the nucleotides 510 to 1736 of SEQ ID NO:5, except that substitution, deletion, or addition of one to 10 amino acids is present in the amino acid sequence of a protein encoded by said DNA, and wherein said DNA codes for a protein having aspartokinase activity.

23. An isolated DNA which codes for a protein selected from the group consisting of:

(A) a protein comprising the amino acid sequence of SEQ ID NO:10, and (B) a protein comprising the amino acid sequence of SEQ ID NO:10 except that substitution, deletion, insertion, or addition of one to 10 amino acids in said amino acid sequence is present, and wherein said protein has dihydrodipicolinate synthase activity.

24. The DNA according to claim 23, wherein said DNA is selected from the group consisting of:

(a) a DNA comprising the nucleotides 1268 to 2155 of SEQ ID NO:9; and (b) a DNA having the nucleotides 1268 to 2155 of SEQ ID NO:9 except that substitution, deletion, or addition of one to 10 amino acids is present in the amino acid sequence of a protein encoded by said DNA, and wherein said DNA codes for a protein having dihydrodipicolinate synthase activity.

* * * * *

SEQUENCE LISTING

```
<160> NUMBER OF SEQ ID NOS: 20

<210> SEQ ID NO 1
<211> LENGTH: 1197
<212> TYPE: DNA
<213> ORGANISM: Escherichia coli
<220> FEATURE:
<221> NAME/KEY: CDS
<222> LOCATION: (272)..(1147)
<223> OTHER INFORMATION:

<400> SEQUENCE: 1

ccaggcgact gtcttcaata ttacagccgc aactactgac atgacgggtg atggtgttca     60

caattccacg gcgatcggca cccaacgcag tgatcaccag ataatgtgtt gcgatgacag    120

tgtcaaactg gttattcctt taaggggtga gttgttctta aggaaagcat aaaaaaaaca    180

tgcatacaac aatcagaacg gttctgtctg cttgctttta atgccatacc aaacgtacca    240

ttgagacact tgtttgcaca gaggatggcc c atg ttc acg gga agt att gtc       292
                                   Met Phe Thr Gly Ser Ile Val
                                   1               5

gcg att gtt act ccg atg gat gaa aaa ggt aat gtc tgt cgg gct agc      340
Ala Ile Val Thr Pro Met Asp Glu Lys Gly Asn Val Cys Arg Ala Ser
        10                  15                  20

ttg aaa aaa ctg att gat tat cat gtc gcc agc ggt act tcg gcg atc      388
Leu Lys Lys Leu Ile Asp Tyr His Val Ala Ser Gly Thr Ser Ala Ile
    25                  30                  35

gtt tct gtt ggc acc act ggc gag tcc gct acc tta aat cat gac gaa      436
Val Ser Val Gly Thr Thr Gly Glu Ser Ala Thr Leu Asn His Asp Glu
40                  45                  50                  55

cat gct gat gtg gtg atg atg acg ctg gat ctg gct gat ggg cgc att      484
His Ala Asp Val Val Met Met Thr Leu Asp Leu Ala Asp Gly Arg Ile
                60                  65                  70
```

-continued ccg gta att gcc ggg acc ggc gct aac gct act gcg gaa gcc att agc 532
Pro Val Ile Ala Gly Thr Gly Ala Asn Ala Thr Ala Glu Ala Ile Ser
75 80 85 ctg acg cag cgc ttc aat gac agt ggt atc gtc ggc tgc ctg acg gta 580
Leu Thr Gln Arg Phe Asn Asp Ser Gly Ile Val Gly Cys Leu Thr Val
90 95 100 acc cct tac tac aat cgt ccg tcg caa gaa ggt ttg tat cag cat ttc 628
Thr Pro Tyr Tyr Asn Arg Pro Ser Gln Glu Gly Leu Tyr Gln His Phe
105 110 115 aaa gcc atc gct gag cat act gac ctg ccg caa att ctg tat aat gtg 676
Lys Ala Ile Ala Glu His Thr Asp Leu Pro Gln Ile Leu Tyr Asn Val
120 125 130 135 ccg tcc cgt act ggc tgc gat ctg ctc ccg gaa acg gtg ggc cgt ctg 724
Pro Ser Arg Thr Gly Cys Asp Leu Leu Pro Glu Thr Val Gly Arg Leu
140 145 150 gcg aaa gta aaa aat att atc gga atc aaa gag gca aca ggg aac tta 772
Ala Lys Val Lys Asn Ile Ile Gly Ile Lys Glu Ala Thr Gly Asn Leu
155 160 165 acg cgt gta aac cag atc aaa gag ctg gtt tca gat gat ttt gtt ctg 820
Thr Arg Val Asn Gln Ile Lys Glu Leu Val Ser Asp Asp Phe Val Leu
170 175 180 ctg agc ggc gat gat gcg agc gcg ctg gac ttc atg caa ttg ggc ggt 868
Leu Ser Gly Asp Asp Ala Ser Ala Leu Asp Phe Met Gln Leu Gly Gly
185 190 195 cat ggg gtt att tcc gtt acg act aac gtc gca gcg cgt gat atg gcc 916
His Gly Val Ile Ser Val Thr Thr Asn Val Ala Ala Arg Asp Met Ala
200 205 210 215 cag atg tgc aaa ctg gca gca gaa gaa cat ttt gcc gag gca cgc gtt 964
Gln Met Cys Lys Leu Ala Ala Glu Glu His Phe Ala Glu Ala Arg Val
220 225 230 att aat cag cgt ctg atg cca tta cac aac aaa cta ttt gtc gaa ccc 1012
Ile Asn Gln Arg Leu Met Pro Leu His Asn Lys Leu Phe Val Glu Pro
235 240 245 aat cca atc ccg gtg aaa tgg gca tgt aag gaa ctg ggt ctt gtg gcg 1060
Asn Pro Ile Pro Val Lys Trp Ala Cys Lys Glu Leu Gly Leu Val Ala
250 255 260 acc gat acg ctg cgc ctg cca atg aca cca atc acc gac agt ggt cgt 1108
Thr Asp Thr Leu Arg Leu Pro Met Thr Pro Ile Thr Asp Ser Gly Arg
265 270 275 gag acg gtc aga gcg gcg ctt aag cat gcc ggt ttg ctg taaagtttag 1157
Glu Thr Val Arg Ala Ala Leu Lys His Ala Gly Leu Leu
280 285 290 ggagatttga tggcttactc tgttcaaaag tcgcgcctgg 1197

<210> SEQ ID NO 2
<211> LENGTH: 292
<212> TYPE: PRT
<213> ORGANISM: Escherichia coli

<400> SEQUENCE: 2

Met Phe Thr Gly Ser Ile Val Ala Ile Val Thr Pro Met Asp Glu Lys
1 5 10 15

Gly Asn Val Cys Arg Ala Ser Leu Lys Lys Leu Ile Asp Tyr His Val
20 25 30

Ala Ser Gly Thr Ser Ala Ile Val Ser Val Gly Thr Thr Gly Glu Ser
35 40 45

Ala Thr Leu Asn His Asp Glu His Ala Asp Val Val Met Met Thr Leu
50 55 60

-continued

```
Asp Leu Ala Asp Gly Arg Ile Pro Val Ile Ala Gly Thr Gly Ala Asn
65                  70                  75                  80

Ala Thr Ala Glu Ala Ile Ser Leu Thr Gln Arg Phe Asn Asp Ser Gly
                85                  90                  95

Ile Val Gly Cys Leu Thr Val Thr Pro Tyr Tyr Asn Arg Pro Ser Gln
            100                 105                 110

Glu Gly Leu Tyr Gln His Phe Lys Ala Ile Ala Glu His Thr Asp Leu
        115                 120                 125

Pro Gln Ile Leu Tyr Asn Val Pro Ser Arg Thr Gly Cys Asp Leu Leu
    130                 135                 140

Pro Glu Thr Val Gly Arg Leu Ala Lys Val Lys Asn Ile Ile Gly Ile
145                 150                 155                 160

Lys Glu Ala Thr Gly Asn Leu Thr Arg Val Asn Gln Ile Lys Glu Leu
                165                 170                 175

Val Ser Asp Asp Phe Val Leu Leu Ser Gly Asp Asp Ala Ser Ala Leu
            180                 185                 190

Asp Phe Met Gln Leu Gly Gly His Gly Val Ile Ser Val Thr Thr Asn
        195                 200                 205

Val Ala Ala Arg Asp Met Ala Gln Met Cys Lys Leu Ala Ala Glu Glu
    210                 215                 220

His Phe Ala Glu Ala Arg Val Ile Asn Gln Arg Leu Met Pro Leu His
225                 230                 235                 240

Asn Lys Leu Phe Val Glu Pro Asn Pro Ile Pro Val Lys Trp Ala Cys
                245                 250                 255

Lys Glu Leu Gly Leu Val Ala Thr Asp Thr Leu Arg Leu Pro Met Thr
            260                 265                 270

Pro Ile Thr Asp Ser Gly Arg Glu Thr Val Arg Ala Ala Leu Lys His
        275                 280                 285

Ala Gly Leu Leu
    290


<210> SEQ ID NO 3
<211> LENGTH: 2147
<212> TYPE: DNA
<213> ORGANISM: Escherichia coli
<220> FEATURE:
<221> NAME/KEY: CDS
<222> LOCATION: (584)..(1930)
<223> OTHER INFORMATION:

<400> SEQUENCE: 3

tcgaagtgtt tctgtagtgc ctgccaggca gcggtctgcg ttggattgat gtttttcatt      60

agcaatactc ttctgatttt gagaattgtg actttggaag attgtagcgc cagtcacaga     120

aaaatgtgat ggttttagtg ccgttagcgt aatgttgagt gtaaaccctt agcgcagtga     180

agcatttatt agctgaacta ctgaccgcca ggagtggatg aaaaatccgc atgaccccat     240

cgttgacaac cgccccgctc accctttatt tataaatgta ctacctgcgc tagcgcaggc     300

cagaagaggc gcgttgccca agtaacggtg ttggaggagc cagtcctgtg ataacacctg     360

agggggtgca tcgccgaggt gattgaacgg ctggccacgt tcatcatcgg ctaagggggc     420

tgaatcccct gggttgtcac cagaagcgtt cgcagtcggg cgtttcgcaa gtggtggagc     480

acttctgggt gaaaatagta gcgaagtatc gctctgcgcc cacccgtctt ccgctcttcc     540

cttgtgccaa ggctgaaaat ggatcccctg acacgaggta gtt atg tct gaa att      595
                                                Met Ser Glu Ile
                                                1
```

-continued

```
gtt gtc tcc aaa ttt ggc ggt acc agc gta gct gat ttt gac gcc atg      643
Val Val Ser Lys Phe Gly Gly Thr Ser Val Ala Asp Phe Asp Ala Met
5                   10                  15                  20

aac cgc agc gct gat att gtg ctt tct gat gcc aac gtg cgt tta gtt      691
Asn Arg Ser Ala Asp Ile Val Leu Ser Asp Ala Asn Val Arg Leu Val
                25                  30                  35

gtc ctc tcg gct tct gct ggt atc act aat ctg ctg gtc gct tta gct      739
Val Leu Ser Ala Ser Ala Gly Ile Thr Asn Leu Leu Val Ala Leu Ala
            40                  45                  50

gaa gga ctg gaa cct ggc gag cga ttc gaa aaa ctc gac gct atc cgc      787
Glu Gly Leu Glu Pro Gly Glu Arg Phe Glu Lys Leu Asp Ala Ile Arg
        55                  60                  65

aac atc cag ttt gcc att ctg gaa cgt ctg cgt tac ccg aac gtt atc      835
Asn Ile Gln Phe Ala Ile Leu Glu Arg Leu Arg Tyr Pro Asn Val Ile
    70                  75                  80

cgt gaa gag att gaa cgt ctg ctg gag aac att act gtt ctg gca gaa      883
Arg Glu Glu Ile Glu Arg Leu Leu Glu Asn Ile Thr Val Leu Ala Glu
85                  90                  95                  100

gcg gcg gcg ctg gca acg tct ccg gcg ctg aca gat gag ctg gtc agc      931
Ala Ala Ala Leu Ala Thr Ser Pro Ala Leu Thr Asp Glu Leu Val Ser
                105                 110                 115

cac ggc gag ctg atg tcg acc ctg ctg ttt gtt gag atc ctg cgc gaa      979
His Gly Glu Leu Met Ser Thr Leu Leu Phe Val Glu Ile Leu Arg Glu
            120                 125                 130

cgc gat gtt cag gca cag tgg ttt gat gta cgt aaa gtg atg cgt acc     1027
Arg Asp Val Gln Ala Gln Trp Phe Asp Val Arg Lys Val Met Arg Thr
        135                 140                 145

aac gac cga ttt ggt cgt gca gag cca gat ata gcc gcg ctg gcg gaa     1075
Asn Asp Arg Phe Gly Arg Ala Glu Pro Asp Ile Ala Ala Leu Ala Glu
    150                 155                 160

ctg gcc gcg ctg cag ctg ctc cca cgt ctc aat gaa ggc tta gtg atc     1123
Leu Ala Ala Leu Gln Leu Leu Pro Arg Leu Asn Glu Gly Leu Val Ile
165                 170                 175                 180

acc cag gga ttt atc ggt agc gaa aat aaa ggt cgt aca acg acg ctt     1171
Thr Gln Gly Phe Ile Gly Ser Glu Asn Lys Gly Arg Thr Thr Thr Leu
                185                 190                 195

ggc cgt gga ggc agc gat tat acg gca gcc ttg ctg gcg gag gct tta     1219
Gly Arg Gly Gly Ser Asp Tyr Thr Ala Ala Leu Leu Ala Glu Ala Leu
            200                 205                 210

cac gca tct cgt gtt gat atc tgg acc gac gtc ccg ggc atc tac acc     1267
His Ala Ser Arg Val Asp Ile Trp Thr Asp Val Pro Gly Ile Tyr Thr
        215                 220                 225

acc gat cca cgc gta gtt tcc gca gca aaa cgc att gat gaa atc gcg     1315
Thr Asp Pro Arg Val Val Ser Ala Ala Lys Arg Ile Asp Glu Ile Ala
    230                 235                 240

ttt gcc gaa gcg gca gag atg gca act ttt ggt gca aaa gta ctg cat     1363
Phe Ala Glu Ala Ala Glu Met Ala Thr Phe Gly Ala Lys Val Leu His
245                 250                 255                 260

ccg gca acg ttg cta ccc gca gta cgc agc gat atc ccg gtc ttt gtc     1411
Pro Ala Thr Leu Leu Pro Ala Val Arg Ser Asp Ile Pro Val Phe Val
                265                 270                 275

ggc tcc agc aaa gac cca cgc gca ggt ggt acg ctg gtg tgc aat aaa     1459
Gly Ser Ser Lys Asp Pro Arg Ala Gly Gly Thr Leu Val Cys Asn Lys
            280                 285                 290

act gaa aat ccg ccg ctg ttc cgc gct ctg gcg ctt cgt cgc aat cag     1507
Thr Glu Asn Pro Pro Leu Phe Arg Ala Leu Ala Leu Arg Arg Asn Gln
        295                 300                 305

act ctg ctc act ttg cac agc ctg aat atg ctg cat tct cgc ggt ttc     1555
Thr Leu Leu Thr Leu His Ser Leu Asn Met Leu His Ser Arg Gly Phe
    310                 315                 320
```

-continued

```
ctc gcg gaa gtt ttc ggc atc ctc gcg cgg cat aat att tcg gta gac      1603
Leu Ala Glu Val Phe Gly Ile Leu Ala Arg His Asn Ile Ser Val Asp
325                 330                 335                 340

tta atc acc acg tca gaa gtg agc gtg gca tta acc ctt gat acc acc      1651
Leu Ile Thr Thr Ser Glu Val Ser Val Ala Leu Thr Leu Asp Thr Thr
                345                 350                 355

ggt tca acc tcc act ggc gat acg ttg ctg acg caa tct ctg ctg atg      1699
Gly Ser Thr Ser Thr Gly Asp Thr Leu Leu Thr Gln Ser Leu Leu Met
            360                 365                 370

gag ctt tcc gca ctg tgt cgg gtg gag gtg gaa gaa ggt ctg gcg ctg      1747
Glu Leu Ser Ala Leu Cys Arg Val Glu Val Glu Glu Gly Leu Ala Leu
        375                 380                 385

gtc gcg ttg att ggc aat gac ctg tca aaa gcc tgc ggc gtt ggc aaa      1795
Val Ala Leu Ile Gly Asn Asp Leu Ser Lys Ala Cys Gly Val Gly Lys
    390                 395                 400

gag gta ttc ggc gta ctg gaa ccg ttc aac att cgc atg att tgt tat      1843
Glu Val Phe Gly Val Leu Glu Pro Phe Asn Ile Arg Met Ile Cys Tyr
405                 410                 415                 420

ggc gca tcc agc cat aac ctg tgc ttc ctg gtg ccc ggc gaa gat gcc      1891
Gly Ala Ser Ser His Asn Leu Cys Phe Leu Val Pro Gly Glu Asp Ala
                425                 430                 435

gag cag gtg gtg caa aaa ctg cat agt aat ttg ttt gag taaatactgt       1940
Glu Gln Val Val Gln Lys Leu His Ser Asn Leu Phe Glu
            440                 445

atggcctgga agctatattt cgggccgtat tgattttctt gtcactatgc tcatcaataa   2000

acgagcctgt actctgttaa ccagcgtctt tatcggagaa taattgcctt taattttttt   2060

atctgcatct ctaattaatt atcgaaagag ataaatagtt aagagaaggc aaaatgaata   2120

ttatcagttc tgctcgcaaa ggaattc                                        2147


<210> SEQ ID NO 4
<211> LENGTH: 449
<212> TYPE: PRT
<213> ORGANISM: Escherichia coli

<400> SEQUENCE: 4

Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Glu Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160
```

-continued

```
Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu
        275                 280                 285

Val Cys Asn Lys Thr Glu Asn Pro Pro Leu Phe Arg Ala Leu Ala Leu
    290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
            340                 345                 350

Leu Asp Thr Thr Gly Ser Thr Ser Thr Gly Asp Thr Leu Leu Thr Gln
        355                 360                 365

Ser Leu Leu Met Glu Leu Ser Ala Leu Cys Arg Val Glu Val Glu Glu
    370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
            420                 425                 430

Gly Glu Asp Ala Glu Gln Val Val Gln Lys Leu His Ser Asn Leu Phe
        435                 440                 445

Glu


<210> SEQ ID NO 5
<211> LENGTH: 1981
<212> TYPE: DNA
<213> ORGANISM: Methylophilus methylotrophus
<220> FEATURE:
<221> NAME/KEY: CDS
<222> LOCATION: (510)..(1736)
<223> OTHER INFORMATION:

<400> SEQUENCE: 5

gtttaacgcg gccagtgaat ttgactcggt cccctgcctg gcaaaatcgc acaggtgatg      60

gacaacgtga aatcgcttga aaaagaattg gcacgcctca agtccaagct ggcctcctca     120

cagggggatg acctcgcgac gcaagcgcag gacgtcaacg gcgccaaagt actggcagcc     180

accctcgacg gggcggatgc caatgccttg cgtgaaacca tggataagct caaagataaa     240

ctcaaatctg cagtcattgt gctggcgagc gtggctgacg gtaaagtcag cctggctgcg     300

ggtgtcacta ctgacttgac tggcaaggtc aaagcaggcg aagttggtca atcatgtggc     360
```

-continued

```
tggtcaggtc ggtggcaaag gtggtggtaa accggatatg gcgatggcag gtggtactga    420

gcccgctaat ttgccgcagg ctttggcaag tgtgaaggct tgggtagaaa caaaactaaa    480

ttaatttaat tgattaacag agcgaaata atg gca tta atc gta caa aaa tat      533
                                Met Ala Leu Ile Val Gln Lys Tyr
                                1               5

ggt ggt acc tcg gtg gct aat ccc gag cgt atc cgt aat gtg gcg cgt      581
Gly Gly Thr Ser Val Ala Asn Pro Glu Arg Ile Arg Asn Val Ala Arg
    10                  15                  20

cgc gtg gcg cgt tac aag gca ttg ggc cac cag gtg gtg gtt gtg gta      629
Arg Val Ala Arg Tyr Lys Ala Leu Gly His Gln Val Val Val Val Val
25                  30                  35                  40

tcc gca atg tct ggt gaa acc aac cgg ttg atc tca ctg gcc aag gaa      677
Ser Ala Met Ser Gly Glu Thr Asn Arg Leu Ile Ser Leu Ala Lys Glu
                45                  50                  55

atc atg caa gac cct gat cca cgt gag ctg gat gtg atg gta tca acc      725
Ile Met Gln Asp Pro Asp Pro Arg Glu Leu Asp Val Met Val Ser Thr
            60                  65                  70

ggt gag cag gtc acc atc ggc atg acg gcc ctg gca ctg atg gag ctt      773
Gly Glu Gln Val Thr Ile Gly Met Thr Ala Leu Ala Leu Met Glu Leu
        75                  80                  85

ggc att aag gca aaa agc tat acc ggt acc cag gtt aag atc ttg act      821
Gly Ile Lys Ala Lys Ser Tyr Thr Gly Thr Gln Val Lys Ile Leu Thr
    90                  95                  100

gac gat gct ttt acc aag gca cgt att ctg gat atc gac gaa cat aac      869
Asp Asp Ala Phe Thr Lys Ala Arg Ile Leu Asp Ile Asp Glu His Asn
105                 110                 115                 120

ctg aaa aaa gac ctg gat gat ggc tat gtc tgc gtg gtg gct ggg ttc      917
Leu Lys Lys Asp Leu Asp Asp Gly Tyr Val Cys Val Val Ala Gly Phe
                125                 130                 135

cag ggc gtg gat gcc aat ggc aat att acg acc ttg ggc cgt ggc ggc      965
Gln Gly Val Asp Ala Asn Gly Asn Ile Thr Thr Leu Gly Arg Gly Gly
            140                 145                 150

tca gat act act ggt gta gca ctg gct gcg gcg tta aag gcg gat gaa     1013
Ser Asp Thr Thr Gly Val Ala Leu Ala Ala Ala Leu Lys Ala Asp Glu
        155                 160                 165

tgt cag att tat acc gat gtc gat ggc gtt tac acc acc gat ccg cgt     1061
Cys Gln Ile Tyr Thr Asp Val Asp Gly Val Tyr Thr Thr Asp Pro Arg
    170                 175                 180

gtg gtg cct gag gca cgc cgc ttg gat aaa att acc ttt gaa gaa atg     1109
Val Val Pro Glu Ala Arg Arg Leu Asp Lys Ile Thr Phe Glu Glu Met
185                 190                 195                 200

ttg gaa ctg gct tca cag ggc tcc aaa gta ttg caa att cgc tcg gtt     1157
Leu Glu Leu Ala Ser Gln Gly Ser Lys Val Leu Gln Ile Arg Ser Val
                205                 210                 215

gag ttt gcc ggt aaa tac aaa gtc aaa tta cgt gtg ctg tcc agc ttc     1205
Glu Phe Ala Gly Lys Tyr Lys Val Lys Leu Arg Val Leu Ser Ser Phe
            220                 225                 230

gaa gag gag ggc gac ggt aca ctg atc aca ttc gaa gaa aat gag gaa     1253
Glu Glu Glu Gly Asp Gly Thr Leu Ile Thr Phe Glu Glu Asn Glu Glu
        235                 240                 245

aac atg gaa gaa cca att atc tcc ggc atc gcc ttt aac cgc gat gag     1301
Asn Met Glu Glu Pro Ile Ile Ser Gly Ile Ala Phe Asn Arg Asp Glu
    250                 255                 260

gcg aaa att acc gtg acg ggc gtg ccc gac aaa cca gga att gcc tat     1349
Ala Lys Ile Thr Val Thr Gly Val Pro Asp Lys Pro Gly Ile Ala Tyr
265                 270                 275                 280

cag att ttg ggc ccg gtg gca gac gcc aat att gat gtg gat atg att     1397
Gln Ile Leu Gly Pro Val Ala Asp Ala Asn Ile Asp Val Asp Met Ile
```

-continued

```
                285                 290                 295

atc cag aac gtc ggt gcg gat ggt acg act gac ttc acc ttt acc gta     1445
Ile Gln Asn Val Gly Ala Asp Gly Thr Thr Asp Phe Thr Phe Thr Val
            300                 305                 310

cat aaa aat gag atg aac aaa gcc ctg agc att ctt aga gat aaa gtg     1493
His Lys Asn Glu Met Asn Lys Ala Leu Ser Ile Leu Arg Asp Lys Val
        315                 320                 325

cag ggc cat atc cag gca cgt gaa atc agc ggc gac gac aag att gcc     1541
Gln Gly His Ile Gln Ala Arg Glu Ile Ser Gly Asp Asp Lys Ile Ala
    330                 335                 340

aaa gtc tct gtg gtt ggg gtg ggt atg cgc tca cat gta ggg atc gcc     1589
Lys Val Ser Val Val Gly Val Gly Met Arg Ser His Val Gly Ile Ala
345                 350                 355                 360

agc cag atg ttc cgt acg ctg gcc gaa gaa ggg atc aat att caa atg     1637
Ser Gln Met Phe Arg Thr Leu Ala Glu Glu Gly Ile Asn Ile Gln Met
                365                 370                 375

atc tca acc agc gaa att aaa att gca gtc gtg atc gaa gag aag tac     1685
Ile Ser Thr Ser Glu Ile Lys Ile Ala Val Val Ile Glu Glu Lys Tyr
            380                 385                 390

atg gaa ctg gct gta cgc gtg ttg cat aaa gca ttc ggc ctc gaa aac     1733
Met Glu Leu Ala Val Arg Val Leu His Lys Ala Phe Gly Leu Glu Asn
        395                 400                 405

gca taatcgccaa cggacgaata aagaaataaa acattcttct tttttgcgtt          1786
Ala

gatttttgaa gggttttcac gtagtatggc agcccttcga tgcagtagca atgctgcaaa   1846

gagaacagca tgccgctgtg ttggtactat taaaacttca ttgttttaat aaggtgaggg   1906

ggatcctcta gagtcgacct gcaggcatgc aagcttggcc gtaatccatg gtcatagctg   1966

tttcctggtg tgaaa                                                    1981


<210> SEQ ID NO 6
<211> LENGTH: 409
<212> TYPE: PRT
<213> ORGANISM: Methylophilus methylotrophus

<400> SEQUENCE: 6

Met Ala Leu Ile Val Gln Lys Tyr Gly Gly Thr Ser Val Ala Asn Pro
1               5                   10                  15

Glu Arg Ile Arg Asn Val Ala Arg Arg Val Ala Arg Tyr Lys Ala Leu
            20                  25                  30

Gly His Gln Val Val Val Val Val Ser Ala Met Ser Gly Glu Thr Asn
        35                  40                  45

Arg Leu Ile Ser Leu Ala Lys Glu Ile Met Gln Asp Pro Asp Pro Arg
    50                  55                  60

Glu Leu Asp Val Met Val Ser Thr Gly Glu Gln Val Thr Ile Gly Met
65                  70                  75                  80

Thr Ala Leu Ala Leu Met Glu Leu Gly Ile Lys Ala Lys Ser Tyr Thr
                85                  90                  95

Gly Thr Gln Val Lys Ile Leu Thr Asp Asp Ala Phe Thr Lys Ala Arg
            100                 105                 110

Ile Leu Asp Ile Asp Glu His Asn Leu Lys Lys Asp Leu Asp Asp Gly
        115                 120                 125

Tyr Val Cys Val Val Ala Gly Phe Gln Gly Val Asp Ala Asn Gly Asn
    130                 135                 140

Ile Thr Thr Leu Gly Arg Gly Gly Ser Asp Thr Thr Gly Val Ala Leu
145                 150                 155                 160
```

-continued

```
Ala Ala Ala Leu Lys Ala Asp Glu Cys Gln Ile Tyr Thr Asp Val Asp
                165                 170                 175

Gly Val Tyr Thr Thr Asp Pro Arg Val Val Pro Glu Ala Arg Arg Leu
            180                 185                 190

Asp Lys Ile Thr Phe Glu Glu Met Leu Glu Leu Ala Ser Gln Gly Ser
        195                 200                 205

Lys Val Leu Gln Ile Arg Ser Val Glu Phe Ala Gly Lys Tyr Lys Val
    210                 215                 220

Lys Leu Arg Val Leu Ser Ser Phe Glu Glu Glu Gly Asp Gly Thr Leu
225                 230                 235                 240

Ile Thr Phe Glu Glu Asn Glu Glu Asn Met Glu Glu Pro Ile Ile Ser
                245                 250                 255

Gly Ile Ala Phe Asn Arg Asp Glu Ala Lys Ile Thr Val Thr Gly Val
            260                 265                 270

Pro Asp Lys Pro Gly Ile Ala Tyr Gln Ile Leu Gly Pro Val Ala Asp
        275                 280                 285

Ala Asn Ile Asp Val Asp Met Ile Ile Gln Asn Val Gly Ala Asp Gly
    290                 295                 300

Thr Thr Asp Phe Thr Phe Thr Val His Lys Asn Glu Met Asn Lys Ala
305                 310                 315                 320

Leu Ser Ile Leu Arg Asp Lys Val Gln Gly His Ile Gln Ala Arg Glu
                325                 330                 335

Ile Ser Gly Asp Asp Lys Ile Ala Lys Val Ser Val Val Gly Val Gly
            340                 345                 350

Met Arg Ser His Val Gly Ile Ala Ser Gln Met Phe Arg Thr Leu Ala
        355                 360                 365

Glu Glu Gly Ile Asn Ile Gln Met Ile Ser Thr Ser Glu Ile Lys Ile
    370                 375                 380

Ala Val Val Ile Glu Glu Lys Tyr Met Glu Leu Ala Val Arg Val Leu
385                 390                 395                 400

His Lys Ala Phe Gly Leu Glu Asn Ala
                405
```

```
<210> SEQ ID NO 7
<211> LENGTH: 1452
<212> TYPE: DNA
<213> ORGANISM: Methylophilus methylotrophus
<220> FEATURE:
<221> NAME/KEY: CDS
<222> LOCATION: (98)..(1207)
<223> OTHER INFORMATION:
<221> NAME/KEY: misc_feature
<222> LOCATION: (839)..(839)
<223> OTHER INFORMATION: n =  a, c, or g

<400> SEQUENCE: 7

gcatgcccgc aggtcgactc tagaggatcc ccctgttcaa aaatcttcca aataatcact      60

gtaatgccgg gttgtccggc tgaaatatcg agtcact atg tta aaa gta ggg ttt     115
                                         Met Leu Lys Val Gly Phe
                                         1               5

gta ggc tgg cgt ggc atg gtt gga tcc gtg cta atg cag cgc atg atg      163
Val Gly Trp Arg Gly Met Val Gly Ser Val Leu Met Gln Arg Met Met
            10                  15                  20

cag gaa aac gat ttt gcg gat att gaa ccg caa ttc ttt acg acc tca      211
Gln Glu Asn Asp Phe Ala Asp Ile Glu Pro Gln Phe Phe Thr Thr Ser
        25                  30                  35

caa acg gga ggg gct gcg cct aaa gtt gga aaa gat act cct gcg ctg      259
Gln Thr Gly Gly Ala Ala Pro Lys Val Gly Lys Asp Thr Pro Ala Leu
```

-continued

```
    40                  45                  50

aaa gat gcc aag gat att gat gct ttg cgc cag atg gat gtg att gtg        307
Lys Asp Ala Lys Asp Ile Asp Ala Leu Arg Gln Met Asp Val Ile Val
55                  60                  65                  70

acc tgc cag ggt ggc gat tac acg agt gac gtc ttc cca caa ttg cgc        355
Thr Cys Gln Gly Gly Asp Tyr Thr Ser Asp Val Phe Pro Gln Leu Arg
                75                  80                  85

gca acc ggc tgg agc ggc cac tgg att gac gcg gcc tct acc tta cgc        403
Ala Thr Gly Trp Ser Gly His Trp Ile Asp Ala Ala Ser Thr Leu Arg
            90                  95                  100

atg gaa aaa gac tcc gtg atc att tta gac ccg gtg aac atg cat gtg        451
Met Glu Lys Asp Ser Val Ile Ile Leu Asp Pro Val Asn Met His Val
        105                 110                 115

att aaa gat gca ttg tcc aat ggc ggc aaa aac tgg atc ggc ggc aac        499
Ile Lys Asp Ala Leu Ser Asn Gly Gly Lys Asn Trp Ile Gly Gly Asn
    120                 125                 130

tgt acc gtc tca ctt atg ttg atg gcg ctg aat ggc ctg ttt aag gct        547
Cys Thr Val Ser Leu Met Leu Met Ala Leu Asn Gly Leu Phe Lys Ala
135                 140                 145                 150

gac ctg gtc gag tgg gcc act tcc atg acc tac cag gcg gct tca ggc        595
Asp Leu Val Glu Trp Ala Thr Ser Met Thr Tyr Gln Ala Ala Ser Gly
                155                 160                 165

gca ggc gcg cag aat atg cgt gaa ctg att agc cag atg ggc gta gtg        643
Ala Gly Ala Gln Asn Met Arg Glu Leu Ile Ser Gln Met Gly Val Val
            170                 175                 180

aat gcc tcc gtg gct gat ttg ctg gcg gat cca gct tct gcc att ttg        691
Asn Ala Ser Val Ala Asp Leu Leu Ala Asp Pro Ala Ser Ala Ile Leu
        185                 190                 195

cag atc gat aaa aca gtg gcg gat acc atc cgt agc gaa gag ttg cct        739
Gln Ile Asp Lys Thr Val Ala Asp Thr Ile Arg Ser Glu Glu Leu Pro
    200                 205                 210

aaa tct aac ttt ggt gtg cca ttg gcg ggc agt ctg atc cca tgg atc        787
Lys Ser Asn Phe Gly Val Pro Leu Ala Gly Ser Leu Ile Pro Trp Ile
215                 220                 225                 230

gac aag gac tta ggg aat ggt caa agt aaa gaa gaa tgg aag ggc ggc        835
Asp Lys Asp Leu Gly Asn Gly Gln Ser Lys Glu Glu Trp Lys Gly Gly
                235                 240                 245

gta nag acc aat aag att tta ggt cgt gaa gcg aac ccg att gtg att        883
Val Xaa Thr Asn Lys Ile Leu Gly Arg Glu Ala Asn Pro Ile Val Ile
            250                 255                 260

gac ggt ttg tgt gta cgt atc ggc gcc atg cgt tgc cat tca caa gcg        931
Asp Gly Leu Cys Val Arg Ile Gly Ala Met Arg Cys His Ser Gln Ala
        265                 270                 275

ttg act atc aag ctg cgc aag gat gtg ccg ctg gat gaa atc aat cag        979
Leu Thr Ile Lys Leu Arg Lys Asp Val Pro Leu Asp Glu Ile Asn Gln
    280                 285                 290

atg ctg gct gaa gcg aac gac tgg gct aaa gtc att ccc aat gag cgt       1027
Met Leu Ala Glu Ala Asn Asp Trp Ala Lys Val Ile Pro Asn Glu Arg
295                 300                 305                 310

gag gtc agt atg cgg gaa ctc acc ccg gca gcg att acc ggc agt ctg       1075
Glu Val Ser Met Arg Glu Leu Thr Pro Ala Ala Ile Thr Gly Ser Leu
                315                 320                 325

gcg acg cca gta ggg cgt ttg cgc aaa ctg gcg atg ggt ggt gaa tac       1123
Ala Thr Pro Val Gly Arg Leu Arg Lys Leu Ala Met Gly Gly Glu Tyr
            330                 335                 340

ttg tcg gca ttt acc gta ggt gac cag ttg tta tgg ggc gct gcc gaa       1171
Leu Ser Ala Phe Thr Val Gly Asp Gln Leu Leu Trp Gly Ala Ala Glu
        345                 350                 355

cct ttg cgc aga atg ttg agg att ctg gtc gaa tct taagtaattg            1217
```

-continued

```
Pro Leu Arg Arg Met Leu Arg Ile Leu Val Glu Ser
    360                 365                 370

tttaagtagc agcccgtaaa gctatgattt atcaataaaa tcatggtctt ttcgggcttt   1277

tgcttttggt gcaatcctgt ttaatggtta ttgtagcctc aaatcctgta tttattgctc   1337

tcaagccgcc tgggtgcgct tgcgtggctg ggtgaatgat gctattttga caaacgccat   1397

gaattactaa gggttaatcg gtgagtaaat ttcaattaaa aaaaatagcc tttgc        1452


<210> SEQ ID NO 8
<211> LENGTH: 370
<212> TYPE: PRT
<213> ORGANISM: Methylophilus methylotrophus
<220> FEATURE:
<221> NAME/KEY: misc_feature
<222> LOCATION: (248)..(248)
<223> OTHER INFORMATION: The 'Xaa' at location 248 stands for Lys, Glu,
      or Gln.
<221> NAME/KEY: misc_feature
<222> LOCATION: (839)..(839)
<223> OTHER INFORMATION: n =  a, c, or g

<400> SEQUENCE: 8

Met Leu Lys Val Gly Phe Val Gly Trp Arg Gly Met Val Gly Ser Val
1               5                   10                  15

Leu Met Gln Arg Met Met Gln Glu Asn Asp Phe Ala Asp Ile Glu Pro
            20                  25                  30

Gln Phe Phe Thr Thr Ser Gln Thr Gly Gly Ala Ala Pro Lys Val Gly
        35                  40                  45

Lys Asp Thr Pro Ala Leu Lys Asp Ala Lys Asp Ile Asp Ala Leu Arg
    50                  55                  60

Gln Met Asp Val Ile Val Thr Cys Gln Gly Gly Asp Tyr Thr Ser Asp
65                  70                  75                  80

Val Phe Pro Gln Leu Arg Ala Thr Gly Trp Ser Gly His Trp Ile Asp
                85                  90                  95

Ala Ala Ser Thr Leu Arg Met Glu Lys Asp Ser Val Ile Ile Leu Asp
            100                 105                 110

Pro Val Asn Met His Val Ile Lys Asp Ala Leu Ser Asn Gly Gly Lys
        115                 120                 125

Asn Trp Ile Gly Gly Asn Cys Thr Val Ser Leu Met Leu Met Ala Leu
    130                 135                 140

Asn Gly Leu Phe Lys Ala Asp Leu Val Glu Trp Ala Thr Ser Met Thr
145                 150                 155                 160

Tyr Gln Ala Ala Ser Gly Ala Gly Ala Gln Asn Met Arg Glu Leu Ile
                165                 170                 175

Ser Gln Met Gly Val Val Asn Ala Ser Val Ala Asp Leu Leu Ala Asp
            180                 185                 190

Pro Ala Ser Ala Ile Leu Gln Ile Asp Lys Thr Val Ala Asp Thr Ile
        195                 200                 205

Arg Ser Glu Glu Leu Pro Lys Ser Asn Phe Gly Val Pro Leu Ala Gly
    210                 215                 220

Ser Leu Ile Pro Trp Ile Asp Lys Asp Leu Gly Asn Gly Gln Ser Lys
225                 230                 235                 240

Glu Glu Trp Lys Gly Gly Val Xaa Thr Asn Lys Ile Leu Gly Arg Glu
                245                 250                 255

Ala Asn Pro Ile Val Ile Asp Gly Leu Cys Val Arg Ile Gly Ala Met
            260                 265                 270

Arg Cys His Ser Gln Ala Leu Thr Ile Lys Leu Arg Lys Asp Val Pro
```

-continued

```
        275                 280                 285

Leu Asp Glu Ile Asn Gln Met Leu Ala Glu Ala Asn Asp Trp Ala Lys
    290                 295                 300

Val Ile Pro Asn Glu Arg Glu Val Ser Met Arg Glu Leu Thr Pro Ala
305                 310                 315                 320

Ala Ile Thr Gly Ser Leu Ala Thr Pro Val Gly Arg Leu Arg Lys Leu
                325                 330                 335

Ala Met Gly Gly Glu Tyr Leu Ser Ala Phe Thr Val Gly Asp Gln Leu
            340                 345                 350

Leu Trp Gly Ala Ala Glu Pro Leu Arg Arg Met Leu Arg Ile Leu Val
        355                 360                 365

Glu Ser
    370


<210> SEQ ID NO 9
<211> LENGTH: 3098
<212> TYPE: DNA
<213> ORGANISM: Methylophilus methylotrophus
<220> FEATURE:
<221> NAME/KEY: CDS
<222> LOCATION: (1268)..(2155)
<223> OTHER INFORMATION:

<400> SEQUENCE: 9

cgtgccaact tgcatgcctg ccggtcgctc tagaggatca attgctggca acatttgagt      60

acattattcg cctttgcatg gtaaaggcct atggtcttga tgtaactttc aagacctgcc     120

agccccaaat ccaggatagc ctgcggtgtg ttggccacct tgaacaattt gcgggtggca     180

atattgacac ctttgtctgt cgcctgtgca gacaagatga cggcaatcag taattcgaac     240

gtggagctat gctccagctc agtggttgga ttggggatgg cttgggccag ccgctcaaat     300

atcgccagtc tttttgtgc attcataaaa cggtttcaat cataggtcac agggtcaacc     360

tgtcttttgc gctttgacgc gcgccatggc tgcggcaatg gcatttttct tgagcacctc     420

agttgagggt gtctcggtcg tagcaagcgt ctggttgcgt ttgctgtagg tttgggcggt     480

ctcccgtttt tcaagggcga ggcgagaaag gcgttgctgg tggcgttgtc tcgctaccgc     540

ggcttcagct tcattcatgg cggtagcccg accgggaatc gtttgcatct gtatgcagtc     600

caccgggcag ggcggtaaac atagctcaca gccagtgcat tcctgggaaa tcaccgtatg     660

catcagtttg gatgcgccca aaatggcatc aacgggacag gcctgtatac acagggtgca     720

gccgatgcat gtttcctcat caatcaaggc caccgctttg ggtttggtga tgccgtgggc     780

cggatttaat gcctggaaag gacgttgcag taatttggca agcgcatgaa tgcccgcttc     840

tcctccaggc ggacattggt tgatattggc ctctccgcgg gcgatcgctt cagcataagg     900

tttgcatccc tcgtaaccgc attggcggca ttgagtttgc ggtaataccg cgtcgatctt     960

tgcaatgagg tcgacaaagc gttctggcag ctcaggcgca gtcccttcga cttcaatcat    1020

gtgatggcag gtgagtctgc attcggtcct ggctaaatag ccgtttaaga tgggttgcta    1080

agagttttat tataaccgaa accttgcttt tcctttggcc gggagctagg cggaaaaagc    1140

ttgccgcagt tgggtgccag tgattttgcc gccgtcttgc gcttgtatcc gtccagatac    1200

agcaagtagg cgcgttcttt ggcgttagac cggataatca gttaaaatat tcgctttatt    1260

cttaaag atg gcg cta ggt atg tta acg ggc agt ttg gtc gca atc gtg      1309
        Met Ala Leu Gly Met Leu Thr Gly Ser Leu Val Ala Ile Val
        1               5                   10

acc ccc atg ttt gaa gat gga cgt ttg gat ctg gac gcc ctc aaa aag      1357
```

-continued

```
Thr Pro Met Phe Glu Asp Gly Arg Leu Asp Leu Asp Ala Leu Lys Lys
15                  20                  25                  30

ctg gtc gac ttt cat gta gag gca ggg aca gat ggt att gtc atc gtt      1405
Leu Val Asp Phe His Val Glu Ala Gly Thr Asp Gly Ile Val Ile Val
                35                  40                  45

ggc acg act ggc gag tcg ccc acg gtg gat gta gat gag cat tgt ctg      1453
Gly Thr Thr Gly Glu Ser Pro Thr Val Asp Val Asp Glu His Cys Leu
            50                  55                  60

ctg atc aaa acc acg atc gag cat gtc gcc aag cgc gtg cca gtc att      1501
Leu Ile Lys Thr Thr Ile Glu His Val Ala Lys Arg Val Pro Val Ile
        65                  70                  75

gcc ggt act ggc gca aat tcc act gct gaa gcc att gaa ctg act gcc      1549
Ala Gly Thr Gly Ala Asn Ser Thr Ala Glu Ala Ile Glu Leu Thr Ala
    80                  85                  90

aag gcc aag gcg ctt ggc gca gac gcc tgc ctg ctg gtg gca ccg tat      1597
Lys Ala Lys Ala Leu Gly Ala Asp Ala Cys Leu Leu Val Ala Pro Tyr
95                  100                 105                 110

tac aac aag ccc tcg caa gag ggt ttg tac cag cac ttt aaa gcc gtg      1645
Tyr Asn Lys Pro Ser Gln Glu Gly Leu Tyr Gln His Phe Lys Ala Val
                115                 120                 125

gct gag gcg gtc gat att ccg caa att ctc tat aat gtg cca ggc cgc      1693
Ala Glu Ala Val Asp Ile Pro Gln Ile Leu Tyr Asn Val Pro Gly Arg
            130                 135                 140

acc ggt tgc gac ttg tct aac gac acc gta ttg cgc ctg gcg cag att      1741
Thr Gly Cys Asp Leu Ser Asn Asp Thr Val Leu Arg Leu Ala Gln Ile
        145                 150                 155

cgc aac att gtc ggg att aag gat gcg act gga ggg att gag cgc ggt      1789
Arg Asn Ile Val Gly Ile Lys Asp Ala Thr Gly Gly Ile Glu Arg Gly
    160                 165                 170

acc gat ttg ttg ttg cgt gca cca gct gat ttc gcc att tac agc ggg      1837
Thr Asp Leu Leu Leu Arg Ala Pro Ala Asp Phe Ala Ile Tyr Ser Gly
175                 180                 185                 190

gat gat gcc act gcg ctg gcc ctg atg tta tta ggg ggg aaa ggc gtg      1885
Asp Asp Ala Thr Ala Leu Ala Leu Met Leu Leu Gly Gly Lys Gly Val
                195                 200                 205

att tcg gtc acg gcc aat gtc gcg ccc aaa tta atg cat gaa atg tgc      1933
Ile Ser Val Thr Ala Asn Val Ala Pro Lys Leu Met His Glu Met Cys
            210                 215                 220

gag cat gct ttg aat ggc aac ctg gcc gca gcc aaa gcg gcc aat gcc      1981
Glu His Ala Leu Asn Gly Asn Leu Ala Ala Ala Lys Ala Ala Asn Ala
        225                 230                 235

aaa ctg ttt gca ttg cac cag aag ttg ttt gta gaa gcg aac ccg att      2029
Lys Leu Phe Ala Leu His Gln Lys Leu Phe Val Glu Ala Asn Pro Ile
    240                 245                 250

cca gtg aaa tgg gta tta caa caa atg gga atg att gcc act ggc atc      2077
Pro Val Lys Trp Val Leu Gln Gln Met Gly Met Ile Ala Thr Gly Ile
255                 260                 265                 270

cgt ttg ccg ctg gtc aat tta tcc agc caa tat cat gaa gta ttg cgc      2125
Arg Leu Pro Leu Val Asn Leu Ser Ser Gln Tyr His Glu Val Leu Arg
                275                 280                 285

aac gcc atg aag cag gca gaa att gcc gct tgatcggcta aaactaattt        2175
Asn Ala Met Lys Gln Ala Glu Ile Ala Ala
            290                 295

agggtgaaac aagtgaaata catgagtcat gtttggttac aacgtttggt gctggccagt    2235

ctggtcacag cgctttcagc gtgcgattcc atcccgttta ttgataatag ttctgactac    2295

aagggcgcag gtcgctccag gccacttgaa gtgccgccag acctgaccgc ggtgcgtacc    2355

agcagtactt acaatgtgcc tggtagcacc agttactctg cctatagcca gaaccaggaa    2415
```

-continued

```
gtgcaagagc agaatggtcc acagcctgtg ctcgcagata tgaaaaacgt gcgcatggtg   2475

aaagcaggcc agcagcgttg gctggtggtc aatgcgcctc cggaaaaaat ctggccgatt   2535

gtgcgtgatt tctggctgga tcaaggcttt gctgtcaggg tagagaatcc tgagcttggc   2595

gtgattgaaa ccgagtggtt gcaatctgat gccatcaagc ctaaggaaga taaccgtggc   2655

tatggtgaaa agtttgatgc ctggctggat aaactttctg gttttgccga caggcgtaaa   2715

ttccgtacgc gtctggaacg tggggagaaa gacggcacca ccgaaatcta tatgacgcac   2775

cgtactgtcg ccggtgcacc ggatgatggc aaaaattatg tgcagaccca attgggtgtc   2835

attgataccg gttatcgccc caacgcggct gaaaacaaga acaatgccgg taaagagttt   2895

gatgctgact tggatgcaga attactccgt cgaatgatgg tgaaattagg tctggatgag   2955

cagaaagcag accaggtgat ggcacaatct gcttcagaca agcgtgcaga tgtggtcaag   3015

gagtctgacc agagcgtcac cttgaagttg aatgagccgt ttgaccgtgc ctggcgccgt   3075

gtggcctggc ctggatcccc ggg                                           3098
```

<210> SEQ ID NO 10
<211> LENGTH: 296
<212> TYPE: PRT
<213> ORGANISM: Methylophilus methylotrophus

<400> SEQUENCE: 10

```
Met Ala Leu Gly Met Leu Thr Gly Ser Leu Val Ala Ile Val Thr Pro
1               5                   10                  15

Met Phe Glu Asp Gly Arg Leu Asp Leu Asp Ala Leu Lys Lys Leu Val
            20                  25                  30

Asp Phe His Val Glu Ala Gly Thr Asp Gly Ile Val Ile Val Gly Thr
        35                  40                  45

Thr Gly Glu Ser Pro Thr Val Asp Val Asp Glu His Cys Leu Leu Ile
    50                  55                  60

Lys Thr Thr Ile Glu His Val Ala Lys Arg Val Pro Val Ile Ala Gly
65                  70                  75                  80

Thr Gly Ala Asn Ser Thr Ala Glu Ala Ile Glu Leu Thr Ala Lys Ala
                85                  90                  95

Lys Ala Leu Gly Ala Asp Ala Cys Leu Leu Val Ala Pro Tyr Tyr Asn
            100                 105                 110

Lys Pro Ser Gln Glu Gly Leu Tyr Gln His Phe Lys Ala Val Ala Glu
        115                 120                 125

Ala Val Asp Ile Pro Gln Ile Leu Tyr Asn Val Pro Gly Arg Thr Gly
    130                 135                 140

Cys Asp Leu Ser Asn Asp Thr Val Leu Arg Leu Ala Gln Ile Arg Asn
145                 150                 155                 160

Ile Val Gly Ile Lys Asp Ala Thr Gly Gly Ile Glu Arg Gly Thr Asp
                165                 170                 175

Leu Leu Leu Arg Ala Pro Ala Asp Phe Ala Ile Tyr Ser Gly Asp Asp
            180                 185                 190

Ala Thr Ala Leu Ala Leu Met Leu Leu Gly Gly Lys Gly Val Ile Ser
        195                 200                 205

Val Thr Ala Asn Val Ala Pro Lys Leu Met His Glu Met Cys Glu His
    210                 215                 220

Ala Leu Asn Gly Asn Leu Ala Ala Ala Lys Ala Ala Asn Ala Lys Leu
225                 230                 235                 240

Phe Ala Leu His Gln Lys Leu Phe Val Glu Ala Asn Pro Ile Pro Val
                245                 250                 255
```

-continued

```
Lys Trp Val Leu Gln Gln Met Gly Met Ile Ala Thr Gly Ile Arg Leu
            260                 265                 270

Pro Leu Val Asn Leu Ser Ser Gln Tyr His Glu Val Leu Arg Asn Ala
        275                 280                 285

Met Lys Gln Ala Glu Ile Ala Ala
    290                 295


<210> SEQ ID NO 11
<211> LENGTH: 3390
<212> TYPE: DNA
<213> ORGANISM: Methylophilus methylotrophus
<220> FEATURE:
<221> NAME/KEY: CDS
<222> LOCATION: (2080)..(2883)
<223> OTHER INFORMATION:

<400> SEQUENCE: 11

ccgcaggtcg ctctagagga tcagagttgg acggacaagc tgaagttttg ggagtctgaa     60

gaagctgcgg gcgaagtgat aaagcagctg aatcaactgt agccactgca agcgacgaat    120

gaaagcaaag gcgctgcact cgctaaggat gaggcagccg aatctcagaa aaccacgtca    180

gagcctgtca aggccgagca agaggtattg ccctcggcca ctgcaacaaa taattcagct    240

gctgcagcga cattggctga agaagaagtg gttccctaca ttccggaggg ggagtatcag    300

gctgcaccca ctccagaaga gatggccaag ggtaatctgg atgtcagtga aaaccaggtt    360

actgaggcta aggcacatcc agtgaatgaa aaggaaatgg ctgcccaaat tgcagatacg    420

gttgagccac cacccgtttt tcagcaggaa ccgatggcag aacctattgt agcggctgaa    480

cccgaacccg tattgccacc gcccgtaaaa gccgaaccag ctgtgaagaa tatcacagcg    540

ccagttgttg ccgcagccac tgttgcagcg gcggcaacca agactgctga atctgagtca    600

gttaaatcca aacctgttga tcctaagcct gtggaagcaa aaaccgctgt atcaaaaact    660

gaagtacaaa cacccgcggc acaggcacct gctgcggcag cggccgttga agatgacgag    720

gtcattccat atattcccga aggtgaatat gtggctcctg tcattcctag tgaggccgaa    780

atggttaaag gcaatatggc ggaggcaaat gcacctgcga ctgatgctca agcgcgccag    840

gtaactgaaa aaggggtggc acccacatcg gatgcggcag cagagccatc accgacattt    900

gtcgctgagc aattgccaga accagagcca gaacctgaat tgccaccgcc gcctccgcca    960

tccgtcagca agcctgttgt gagagaggta gcgccagtgg ctgcgctggc agcagaagaa   1020

gagaaaccag tcgctgcgca gcctgagact gagcagccgg ctgccaaggt tgttgagcct   1080

gcatcggtcg cctcccctgt ggcgacgcca gaagcgccag ctggtgatgc tgaaatcaac   1140

caggctgtgg cggcatgggc acaagcttgg cgcagcaagg acattaaaaa ctacctcgct   1200

gcatatgccc ctgacttcat gccagaaggg ttgccttcca gaaaggcatg ggagtcgcaa   1260

cgcaaacagc gtttatctgc aggccagggt gcgattacac tcgtactaaa taatgtgcag   1320

attcagcgtg acggtaccac tgtcgccgtg cagtttgagc aaaaatatgc tgctaaagtt   1380

tataaagatg aattggtcaa aacactggaa atgcgttacg agccaacgca gaaacgttgg   1440

ttgatcacac gtgaacgtgt tgccccttta accggtttgc cagtagcgag tgtgccaacg   1500

acccgtctgc cagcagtcgc tgcagcgtca tccaatacgg atgtggtcga gtcagctgtg   1560

ccaccgacac aatcgacatc atctgcgcct gtagcggaag tgagtgttga atcagcgatt   1620

gacgcctggg cacaggcttg gcgcagtaaa aacatcaatg cttactttgc ggcgtattct   1680

ccagaatttg tgccggaggg attgccaaac agaggtgtct gggaagcgca acgtaaaaag   1740
```

-continued

```
cgcttgtccc cacagcaggg caagatcagc ctggatgtca cgaatgtaag cgtgagccgc   1800

gaaggagaaa cagccgtggc cacctttagg cagaaatatg cgtctaaggc ctatcgtgat   1860

gaagtagtga agcgtctaca gttaaaactg gatgctgcaa gcaatcgctg gctgattgtg   1920

cgtgaaagta ccggtagtga ggcagaagtg ccaatgggca agcagtcagt gagtgcgcca   1980

gaagagagct cggaacatca ggatggtgct ctggagccga tcggatttta atggtctgct   2040

gatgtcgtgg tttaagtatt aaaaataatt gagtgagtt atg ttg aaa gta gtg      2094
                                           Met Leu Lys Val Val
                                           1               5

att gct ggc gtg tct ggt cgt atg gga cat gcc tta ctg gat gga gtt     2142
Ile Ala Gly Val Ser Gly Arg Met Gly His Ala Leu Leu Asp Gly Val
                10                  15                  20

ttt tct gat aac ggc ttg cag ttg cac gcg gca ctc gat cgt gct gaa     2190
Phe Ser Asp Asn Gly Leu Gln Leu His Ala Ala Leu Asp Arg Ala Glu
            25                  30                  35

agc gcc atg ata ggg cgg gat gca ggc gag cag ttt ggc aag gtc agt     2238
Ser Ala Met Ile Gly Arg Asp Ala Gly Glu Gln Phe Gly Lys Val Ser
        40                  45                  50

ggc gtg aaa atc acg gct gac atc cat gcc gca ttg gtc ggt gcc gat     2286
Gly Val Lys Ile Thr Ala Asp Ile His Ala Ala Leu Val Gly Ala Asp
    55                  60                  65

gtg ctg gtg gat ttc acg cgg ccg gaa gcc agt atg caa tat tta caa     2334
Val Leu Val Asp Phe Thr Arg Pro Glu Ala Ser Met Gln Tyr Leu Gln
70                  75                  80                  85

gcc tgc cag caa gcc aac gtt aaa tta gtg att ggt act acc ggg ttt     2382
Ala Cys Gln Gln Ala Asn Val Lys Leu Val Ile Gly Thr Thr Gly Phe
                90                  95                  100

agt gag gca gaa aag gcc agt att gag gct gcg tcc aaa aat atc ggt     2430
Ser Glu Ala Glu Lys Ala Ser Ile Glu Ala Ala Ser Lys Asn Ile Gly
            105                 110                 115

atc gta ttt gct cca aac atg agc gta ggg gtc acc ctc ttg att aac     2478
Ile Val Phe Ala Pro Asn Met Ser Val Gly Val Thr Leu Leu Ile Asn
        120                 125                 130

ctg gtt gag caa gcc gca cgg gtg ctc aat gaa ggc tat gat att gag     2526
Leu Val Glu Gln Ala Ala Arg Val Leu Asn Glu Gly Tyr Asp Ile Glu
    135                 140                 145

gtg gtt gaa atg cat cac cgc cat aag gtg gat gcg cct tca ggc acg     2574
Val Val Glu Met His His Arg His Lys Val Asp Ala Pro Ser Gly Thr
150                 155                 160                 165

gct tta cgg ttg ggt gag gct gcg gca aaa ggg att gat aaa gcg ctt     2622
Ala Leu Arg Leu Gly Glu Ala Ala Ala Lys Gly Ile Asp Lys Ala Leu
                170                 175                 180

aaa gat tgt gct gtg tat gcg cgc gaa ggc gtg act ggt gaa cgc gaa     2670
Lys Asp Cys Ala Val Tyr Ala Arg Glu Gly Val Thr Gly Glu Arg Glu
            185                 190                 195

gcg ggc acg att ggt ttt gca acc tta cgt ggt ggg gat gtg gtc ggt     2718
Ala Gly Thr Ile Gly Phe Ala Thr Leu Arg Gly Gly Asp Val Val Gly
        200                 205                 210

gac cat acg gtg gtt ctg gct ggt gtg ggt gag cga gta gag tta acg     2766
Asp His Thr Val Val Leu Ala Gly Val Gly Glu Arg Val Glu Leu Thr
    215                 220                 225

cat aaa gca tca agc cgt gcc aca ttt gca caa ggt gcg tta cgt gcg     2814
His Lys Ala Ser Ser Arg Ala Thr Phe Ala Gln Gly Ala Leu Arg Ala
230                 235                 240                 245

gct aaa ttt ctg gct gat aaa ccc aag gga ttg ttt gat atg cgt gat     2862
Ala Lys Phe Leu Ala Asp Lys Pro Lys Gly Leu Phe Asp Met Arg Asp
                250                 255                 260
```

-continued

```
gtg ttg gga ttt gaa aag aac tgatctttag taggcgatcc cgtctggcta       2913
Val Leu Gly Phe Glu Lys Asn
            265

aggtctggca ggaatcgtct gatgcttctg agttgccctt gagtgggctg tcaatgtacg   2973

ctataatgct gtaattctga aacgggaaga gtcgaacaag cttttcccgt tttgcacatc   3033

tattcactgc agcttgaatt tcacttccag ccatggtgaa ccctctaaaa gatgtgtttc   3093

gtgtcaaact taaggagcta aaggtgtcaa aaacaattcc agcgattctc gtgttagcag   3153

atggaactgt ttttaagggc attagcattg gcgcttccgg tcatacggta ggtgaggtgg   3213

tgtttaatac ctccatcacc ggttatcagg agattcttac cgatccttcc tataccgaac   3273

aaatcgtgac actgacctat ccgcacattg gtaactacgg gaccaatcgt gaagatggga   3333

gtcaggtaaa gtctatgctg cgggtctgat ccccgggacc gagccgggtt cgtaaag      3390


<210> SEQ ID NO 12
<211> LENGTH: 268
<212> TYPE: PRT
<213> ORGANISM: Methylophilus methylotrophus

<400> SEQUENCE: 12

Met Leu Lys Val Val Ile Ala Gly Val Ser Gly Arg Met Gly His Ala
1               5                   10                  15

Leu Leu Asp Gly Val Phe Ser Asp Asn Gly Leu Gln Leu His Ala Ala
            20                  25                  30

Leu Asp Arg Ala Glu Ser Ala Met Ile Gly Arg Asp Ala Gly Glu Gln
        35                  40                  45

Phe Gly Lys Val Ser Gly Val Lys Ile Thr Ala Asp Ile His Ala Ala
    50                  55                  60

Leu Val Gly Ala Asp Val Leu Val Asp Phe Thr Arg Pro Glu Ala Ser
65                  70                  75                  80

Met Gln Tyr Leu Gln Ala Cys Gln Gln Ala Asn Val Lys Leu Val Ile
                85                  90                  95

Gly Thr Thr Gly Phe Ser Glu Ala Glu Lys Ala Ser Ile Glu Ala Ala
            100                 105                 110

Ser Lys Asn Ile Gly Ile Val Phe Ala Pro Asn Met Ser Val Gly Val
        115                 120                 125

Thr Leu Leu Ile Asn Leu Val Glu Gln Ala Ala Arg Val Leu Asn Glu
    130                 135                 140

Gly Tyr Asp Ile Glu Val Val Glu Met His His Arg His Lys Val Asp
145                 150                 155                 160

Ala Pro Ser Gly Thr Ala Leu Arg Leu Gly Glu Ala Ala Ala Lys Gly
                165                 170                 175

Ile Asp Lys Ala Leu Lys Asp Cys Ala Val Tyr Ala Arg Glu Gly Val
            180                 185                 190

Thr Gly Glu Arg Glu Ala Gly Thr Ile Gly Phe Ala Thr Leu Arg Gly
        195                 200                 205

Gly Asp Val Val Gly Asp His Thr Val Val Leu Ala Gly Val Gly Glu
    210                 215                 220

Arg Val Glu Leu Thr His Lys Ala Ser Ser Arg Ala Thr Phe Ala Gln
225                 230                 235                 240

Gly Ala Leu Arg Ala Ala Lys Phe Leu Ala Asp Lys Pro Lys Gly Leu
                245                 250                 255

Phe Asp Met Arg Asp Val Leu Gly Phe Glu Lys Asn
            260                 265
```

-continued

```
<210> SEQ ID NO 13
<211> LENGTH: 2566
<212> TYPE: DNA
<213> ORGANISM: Methylophilus methylotrophus
<220> FEATURE:
<221> NAME/KEY: CDS
<222> LOCATION: (751)..(1995)
<223> OTHER INFORMATION:
<221> NAME/KEY: misc_feature
<222> LOCATION: (2467)..(2467)
<223> OTHER INFORMATION: n = a, c, g, or t

<400> SEQUENCE: 13

tgctttaggg ggaacctaga ggatccccct acccgaggaa gaagtgagcc aacatgtact      60

tccagtcgta ccatcaaaag tagaagtttt cggcgttatc ctgattcaca gtaaacgaaa     120

aattgcccat attctgaccg gatttaccgg tggcttttaa ggtataagtg gtcgctgact     180

ggttctcaat gctgtaatca aaaaatttgg catcactggg gacacaggca aatcccacat     240

atgtgaagtt gtcctgataa aactgttcgg cctgcacacg gcaattggca agattggcag     300

gcgcttccgc ggcattaccg cttttgatgt aatcctgata gcctggtatg gcgatgctgg     360

ccaagatacc cataatggcc accacgacca tgacttctat caggctgaat ccgtactgat     420

ttgaggactt cattatcaaa ccccttttta gatagcctta tcatgcaaac aggcagctgt     480

catgtccagc atcagccgac caatggtcag gattacccga cgaacggtca aaccactaaa     540

acgcccagtc actggtgcca tgagcaactg caggtttaat gataaaatgg cactcaattt     600

acattggact gtgaacatgt tttccttcta tacgagatta ttggcggttg ccctgctatt     660

ggcacaattg agtgcctgtg gtctcaaagg ggacctgtat attcctgagc gccaataccc     720

tcaaacgcct caacaagata agtcttcatc gtg acc gct ttt tca atc caa caa      774
                                 Val Thr Ala Phe Ser Ile Gln Gln
                                 1               5

ggc cta cta cat gcc gag aat gta gcc ctg cgt gac att gca caa acg       822
Gly Leu Leu His Ala Glu Asn Val Ala Leu Arg Asp Ile Ala Gln Thr
    10                  15                  20

cat caa acg ccc act tac gtc tat tca cgt gcc gcc ttg acg act gct       870
His Gln Thr Pro Thr Tyr Val Tyr Ser Arg Ala Ala Leu Thr Thr Ala
25                  30                  35                  40

ttc gag cgt ttt cag gca ggc ctg act gga cat gac cat ttg atc tgc       918
Phe Glu Arg Phe Gln Ala Gly Leu Thr Gly His Asp His Leu Ile Cys
                45                  50                  55

ttt gct gtc aaa gcc aac cca agc ctg gcc att ctc aac ctg ttt gcg       966
Phe Ala Val Lys Ala Asn Pro Ser Leu Ala Ile Leu Asn Leu Phe Ala
            60                  65                  70

cga atg gga gcg ggc ttt gat att gtg tcc ggt ggt gag ctg gca cgc      1014
Arg Met Gly Ala Gly Phe Asp Ile Val Ser Gly Gly Glu Leu Ala Arg
        75                  80                  85

gtc ttg gcc gca ggt ggc gac ccg aaa aaa gtg gtg ttt tct ggt gtg      1062
Val Leu Ala Ala Gly Gly Asp Pro Lys Lys Val Val Phe Ser Gly Val
    90                  95                  100

ggc aaa tcc cat gcg gaa atc aaa gcc gcg ctt gaa gcg ggc att ctt      1110
Gly Lys Ser His Ala Glu Ile Lys Ala Ala Leu Glu Ala Gly Ile Leu
105                 110                 115                 120

tgc ttc aac gtg gaa tca gtg aat gag cta gac cgc atc cag cag gtg      1158
Cys Phe Asn Val Glu Ser Val Asn Glu Leu Asp Arg Ile Gln Gln Val
                125                 130                 135

gcg gcc agc ctg ggc aaa aaa gcg cct att tcc ctg cgc gtg aac ccc      1206
Ala Ala Ser Leu Gly Lys Lys Ala Pro Ile Ser Leu Arg Val Asn Pro
            140                 145                 150
```

-continued

```
aat gtg gat gcc aaa aca cat ccc tat att tcc cac ccg gct ctc aaa      1254
Asn Val Asp Ala Lys Thr His Pro Tyr Ile Ser His Pro Ala Leu Lys
        155                 160                 165

aac aat aaa ttt ggt gtg gca ttt gaa gat gcc ttg ggc ctc tat gaa      1302
Asn Asn Lys Phe Gly Val Ala Phe Glu Asp Ala Leu Gly Leu Tyr Glu
    170                 175                 180

aaa gcg gcg caa ctg cca aac atc gag gta cac ggc gta gat tgc cat      1350
Lys Ala Ala Gln Leu Pro Asn Ile Glu Val His Gly Val Asp Cys His
185                 190                 195                 200

atc ggc tcg caa atc act gag ctg tca cct ttc ctc gat gcc ttg gat      1398
Ile Gly Ser Gln Ile Thr Glu Leu Ser Pro Phe Leu Asp Ala Leu Asp
                205                 210                 215

aaa gta ttg ggc ctg gta gat gca ttg gcc gcc aaa ggc att cat atc      1446
Lys Val Leu Gly Leu Val Asp Ala Leu Ala Ala Lys Gly Ile His Ile
            220                 225                 230

cag cat ata gac gtt ggc ggc ggt gtc ggt att act tac agc gac gaa      1494
Gln His Ile Asp Val Gly Gly Gly Val Gly Ile Thr Tyr Ser Asp Glu
        235                 240                 245

acg cca cca gac ttt gca gcc tac act gca gcg att ctt aaa aag ctg      1542
Thr Pro Pro Asp Phe Ala Ala Tyr Thr Ala Ala Ile Leu Lys Lys Leu
    250                 255                 260

gca ggc agg aat gta aaa gtg ttg ttt gag ccc ggc cgt gcc ctg gtg      1590
Ala Gly Arg Asn Val Lys Val Leu Phe Glu Pro Gly Arg Ala Leu Val
265                 270                 275                 280

ggt aac gcc ggt gtg ctg ctg acc aag gtc gaa tac ctg aaa cct ggc      1638
Gly Asn Ala Gly Val Leu Leu Thr Lys Val Glu Tyr Leu Lys Pro Gly
                285                 290                 295

gaa acc aaa aac ttt gcg att gtc gat gcc gcc atg aac gac ctc atg      1686
Glu Thr Lys Asn Phe Ala Ile Val Asp Ala Ala Met Asn Asp Leu Met
            300                 305                 310

cgc ccg gct ttg tat gat gct ttc cac aac att acg acc att gcc act      1734
Arg Pro Ala Leu Tyr Asp Ala Phe His Asn Ile Thr Thr Ile Ala Thr
        315                 320                 325

tct gca gcc ccc gca caa atc tat gag atc gtt ggc ccg gtt tgc gag      1782
Ser Ala Ala Pro Ala Gln Ile Tyr Glu Ile Val Gly Pro Val Cys Glu
    330                 335                 340

agt ggt gac ttt tta ggc cat gac cgt aca ctt gcg atc gaa gaa ggt      1830
Ser Gly Asp Phe Leu Gly His Asp Arg Thr Leu Ala Ile Glu Glu Gly
345                 350                 355                 360

gat tac ctg gcg att cac tcc gca ggc gct tat ggc atg agc atg gcc      1878
Asp Tyr Leu Ala Ile His Ser Ala Gly Ala Tyr Gly Met Ser Met Ala
                365                 370                 375

agc aac tac aac acg cgc gcc cgt gcc gca gag gta ttg gtt gat ggt      1926
Ser Asn Tyr Asn Thr Arg Ala Arg Ala Ala Glu Val Leu Val Asp Gly
            380                 385                 390

gac cag gtg cat gtg atc cgt gaa cgt gaa caa att gcc gac ctg ttt      1974
Asp Gln Val His Val Ile Arg Glu Arg Glu Gln Ile Ala Asp Leu Phe
        395                 400                 405

aaa ctg gag cgt acg ctg cca taacattgac ggcaacccct aataaaaaaa        2025
Lys Leu Glu Arg Thr Leu Pro
    410                 415

ccgaagccgc caagcttcgg tttttatta atagcgcatc ctttaatcaa agatcacggt   2085

cttgttcgcg tagagcaaga ttctatgctc aatatgccag cgcacggctt tggaaagcac   2145

aacacgctcc aggtcacggc ctttctggat caggtcttcc acctgatcgc ggtgtgaaat   2205

gcgcgccaag tcctgctcaa taatcggccc ctcatccaac acctctgtca cataatgact   2265

ggtcgcaccg atcagtttca cgccacgctc aaacgcacgg tggtaaggac gtgcgccgat   2325

aaatgctggc aggaatgagt ggtggtgaat gttgataatc cgctgaggat accgtgcgac   2385
```

-continued

```
aaaatctggt gacagaatct gcatgtagcg tgccagcaca atcaggtcaa tcttgtgttg   2445

atcaaacagg gcaaactgct gngcctctac ctctgccttg gtttaccttg gtcatcggta   2505

aatagtgaaa cgggatgcca taaaactgcg ccagggggat cctctgggtc cccctaaagc   2565

a                                                                   2566


<210> SEQ ID NO 14
<211> LENGTH: 415
<212> TYPE: PRT
<213> ORGANISM: Methylophilus methylotrophus
<220> FEATURE:
<221> NAME/KEY: misc_feature
<222> LOCATION: (2467)..(2467)
<223> OTHER INFORMATION: n = a, c, g, or t

<400> SEQUENCE: 14

Val Thr Ala Phe Ser Ile Gln Gln Gly Leu Leu His Ala Glu Asn Val
1               5                   10                  15

Ala Leu Arg Asp Ile Ala Gln Thr His Gln Thr Pro Thr Tyr Val Tyr
            20                  25                  30

Ser Arg Ala Ala Leu Thr Thr Ala Phe Glu Arg Phe Gln Ala Gly Leu
        35                  40                  45

Thr Gly His Asp His Leu Ile Cys Phe Ala Val Lys Ala Asn Pro Ser
    50                  55                  60

Leu Ala Ile Leu Asn Leu Phe Ala Arg Met Gly Ala Gly Phe Asp Ile
65                  70                  75                  80

Val Ser Gly Gly Glu Leu Ala Arg Val Leu Ala Ala Gly Gly Asp Pro
                85                  90                  95

Lys Lys Val Val Phe Ser Gly Val Gly Lys Ser His Ala Glu Ile Lys
            100                 105                 110

Ala Ala Leu Glu Ala Gly Ile Leu Cys Phe Asn Val Glu Ser Val Asn
        115                 120                 125

Glu Leu Asp Arg Ile Gln Gln Val Ala Ala Ser Leu Gly Lys Lys Ala
    130                 135                 140

Pro Ile Ser Leu Arg Val Asn Pro Asn Val Asp Ala Lys Thr His Pro
145                 150                 155                 160

Tyr Ile Ser His Pro Ala Leu Lys Asn Asn Lys Phe Gly Val Ala Phe
                165                 170                 175

Glu Asp Ala Leu Gly Leu Tyr Glu Lys Ala Ala Gln Leu Pro Asn Ile
            180                 185                 190

Glu Val His Gly Val Asp Cys His Ile Gly Ser Gln Ile Thr Glu Leu
        195                 200                 205

Ser Pro Phe Leu Asp Ala Leu Asp Lys Val Leu Gly Leu Val Asp Ala
    210                 215                 220

Leu Ala Ala Lys Gly Ile His Ile Gln His Ile Asp Val Gly Gly Gly
225                 230                 235                 240

Val Gly Ile Thr Tyr Ser Asp Glu Thr Pro Pro Asp Phe Ala Ala Tyr
                245                 250                 255

Thr Ala Ala Ile Leu Lys Lys Leu Ala Gly Arg Asn Val Lys Val Leu
            260                 265                 270

Phe Glu Pro Gly Arg Ala Leu Val Gly Asn Ala Gly Val Leu Leu Thr
        275                 280                 285

Lys Val Glu Tyr Leu Lys Pro Gly Glu Thr Lys Asn Phe Ala Ile Val
    290                 295                 300

Asp Ala Ala Met Asn Asp Leu Met Arg Pro Ala Leu Tyr Asp Ala Phe
```

-continued

```
305                 310                 315                 320

His Asn Ile Thr Thr Ile Ala Thr Ser Ala Ala Pro Ala Gln Ile Tyr
                325                 330                 335

Glu Ile Val Gly Pro Val Cys Glu Ser Gly Asp Phe Leu Gly His Asp
            340                 345                 350

Arg Thr Leu Ala Ile Glu Glu Gly Asp Tyr Leu Ala Ile His Ser Ala
        355                 360                 365

Gly Ala Tyr Gly Met Ser Met Ala Ser Asn Tyr Asn Thr Arg Ala Arg
    370                 375                 380

Ala Ala Glu Val Leu Val Asp Gly Asp Gln Val His Val Ile Arg Glu
385                 390                 395                 400

Arg Glu Gln Ile Ala Asp Leu Phe Lys Leu Glu Arg Thr Leu Pro
                405                 410                 415


<210> SEQ ID NO 15
<211> LENGTH: 39
<212> TYPE: DNA
<213> ORGANISM: Artificial Sequence
<220> FEATURE:
<223> OTHER INFORMATION: Synthetic DNA

<400> SEQUENCE: 15

agggaattcc ccgttctgga taatgttttt tgcgccgac                            39


<210> SEQ ID NO 16
<211> LENGTH: 58
<212> TYPE: DNA
<213> ORGANISM: Artificial Sequence
<220> FEATURE:
<223> OTHER INFORMATION: Synthetic DNA

<400> SEQUENCE: 16

cggatgcatc tagagttaac ctgcagggtg aaattgttat ccgctcacaa ttccacac       58


<210> SEQ ID NO 17
<211> LENGTH: 35
<212> TYPE: DNA
<213> ORGANISM: Artificial Sequence
<220> FEATURE:
<223> OTHER INFORMATION: Synthetic DNA

<400> SEQUENCE: 17

tgacctgcag gtttgcacag aggatggccc atgtt                                35


<210> SEQ ID NO 18
<211> LENGTH: 36
<212> TYPE: DNA
<213> ORGANISM: Artificial Sequence
<220> FEATURE:
<223> OTHER INFORMATION: Synthetic DNA

<400> SEQUENCE: 18

cattctagat ccctaaactt tacagcaaac cggcat                               36


<210> SEQ ID NO 19
<211> LENGTH: 35
<212> TYPE: DNA
<213> ORGANISM: Artificial Sequence
<220> FEATURE:
<223> OTHER INFORMATION: Synthetic DNA

<400> SEQUENCE: 19

gaacctgcag gccctgacac gaggtagatt atgtc                                35
```

-continued

```
<210> SEQ ID NO 20
<211> LENGTH: 55
<212> TYPE: DNA
<213> ORGANISM: Artificial Sequence
<220> FEATURE:
<223> OTHER INFORMATION: Synthetic DNA

<400> SEQUENCE: 20

ctttcggcta gaagagcgag atgcagataa aaaaattaaa ggcaattatt ctccg          55
```